US011384358B2

(12) United States Patent
Debnath et al.

(10) Patent No.: US 11,384,358 B2
(45) Date of Patent: Jul. 12, 2022

(54) METHOD OF REGULATING GENE EXPRESSION IN A CELL

(71) Applicant: President and Fellows of Harvard College, Cambridge, MA (US)

(72) Inventors: Anik Debnath, Boston, MA (US); Javier Fernandez Juarez, Cambridge, MA (US); Henry Hung-yi Lee, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 179 days.

(21) Appl. No.: 16/498,465

(22) PCT Filed: Mar. 29, 2018

(86) PCT No.: PCT/US2018/025154
§ 371 (c)(1),
(2) Date: Sep. 27, 2019

(87) PCT Pub. No.: WO2018/183685
PCT Pub. Date: Oct. 4, 2018

(65) Prior Publication Data
US 2020/0109407 A1 Apr. 9, 2020

Related U.S. Application Data

(60) Provisional application No. 62/478,219, filed on Mar. 29, 2017.

(51) Int. Cl.
| | | |
|---|---|---|
| *C12N 15/63* | (2006.01) | |
| *C12N 1/20* | (2006.01) | |
| *C12N 15/74* | (2006.01) | |
| *C12R 1/23* | (2006.01) | |
| *C12R 1/24* | (2006.01) | |
| *C12R 1/25* | (2006.01) | |
| *C12R 1/245* | (2006.01) | |

(52) U.S. Cl.
CPC ............ *C12N 15/635* (2013.01); *C12N 1/20* (2013.01); *C12N 1/205* (2021.05); *C12N 15/746* (2013.01); *C12R 2001/23* (2021.05); *C12R 2001/24* (2021.05); *C12R 2001/245* (2021.05); *C12R 2001/25* (2021.05)

(58) Field of Classification Search
None
See application file for complete search history.

(56) References Cited

U.S. PATENT DOCUMENTS

| | | |
|---|---|---|
| 5,733,540 A | 3/1998 | Lee |
| 6,372,209 B1 | 4/2002 | Chrisope |
| 7,179,458 B2 | 2/2007 | Chang et al. |
| 8,853,382 B2 | 10/2014 | Hammarstrom et al. |
| 2008/0131402 A1 | 6/2008 | Farrar et al. |
| 2009/0226418 A1 | 9/2009 | Frenken et al. |
| 2010/0143305 A1 | 6/2010 | Lemke |
| 2010/0196956 A1 | 8/2010 | Sung et al. |
| 2011/0104121 A1 | 5/2011 | Wira et al. |
| 2014/0044653 A1 | 2/2014 | Qvit-Raz et al. |
| 2016/0340665 A1 | 11/2016 | Falb et al. |
| 2017/0058282 A1* | 3/2017 | Lu ..................... C07K 14/335 |

FOREIGN PATENT DOCUMENTS

| | | | |
|---|---|---|---|
| CA | 2360022 A1 | 7/2000 | |
| EP | 0759997 B1 | 6/2003 | |
| JP | 2006262724 A | 10/2006 | |
| WO | 2004076615 A2 | 9/2004 | |
| WO | 2014/052438 A1 | 4/2014 | |
| WO | 2016/0168182 A1 | 10/2016 | |
| WO | WO-2016168182 A1 * | 10/2016 | ......... C12N 15/1086 |

OTHER PUBLICATIONS

Heiss et al. 2016 (Evaluation of novel inducible promoter/repressor systems for recombinant protein expression in Lactobacillus plantarum; Microbial Cell Factories 15:50; of record). (Year: 2016).*
McCraken et al., 2000 (Analysis of promoter sequences from Lactobacillus and Lactococcus and their activity in several Lactobacillus species; Arch. Microbiol. 173: 383-389). (Year: 2000).*
Boot et al. 1996 (J. Bacteriol. 177(24): 7222-7230) (Year: 1996).*
Postle 1984 (Nucleotide sequence of the repressor gene of the TN 10 tetracycline resistance determinant; Nucleic Acids Research 12(12):4849-4863). (Year: 1984).*
Heiss et al., "Evaluation of novel inducible promoter/repressor systems for recombinant protein expression in Lactobacillus plantarum," Microbial Cell Factories, vol. 15, No. 1, pp. 1-17 (Mar. 10, 2016).
Steidler, Lothar, et al.,"Treatment of Murine Colitis by Lactococcus lactis Secreting Interleukin-10," Science, Aug. 25, 2000, pp. 1352-1355, vol. 289, The American Association for the Advancement of Science.

(Continued)

*Primary Examiner* — Mary Maille Lyons
(74) *Attorney, Agent, or Firm* — Banner & Witcoff, Ltd.

(57) ABSTRACT

The disclosure provides methods of making a tetracycline inducible expression system in a cell. The methods include providing the cell with a first nucleic acid sequence comprising a first promoter operably linked to a tetracycline repressor gene coding sequence, providing the cell with a second nucleic acid sequence comprising a second promoter operably linked to a coding sequence of a gene of interest wherein the second promoter is modified to include one or more tetracycline repressor protein binding sites, and determining the expression of the gene of interest in the presence or absence of tetracycline. The disclosure further provides nucleic acid sequences, vectors and cells including the tetracycline inducible modified promoter.

25 Claims, 17 Drawing Sheets
Specification includes a Sequence Listing.

(56) References Cited

OTHER PUBLICATIONS

Vandenbroucke, K., et al.,"Orally administered L. lactis secreting an anti-TNF Nanobody demonstrate efficacy in chronic colitis," Nature, Jan. 2010, pp. 49-56, vol. 3, No. 1, Nature Publishing Group.

Marcobal, Angela, et al.,"Expression of Human Immunodeficiency Virus Type 1 Neutralizing Antibody Fragments Using Human Vaginal Lactobacillus," Aids Research and Human Retroviruses, 2016, pp. 964-971, vol. 32, No. 10/11, Mary Ann Liebert, Inc.

International Search Report and Written Opinion of PCT/US2018/025154 dated Jul. 26, 2018.

* cited by examiner

FIG. 1

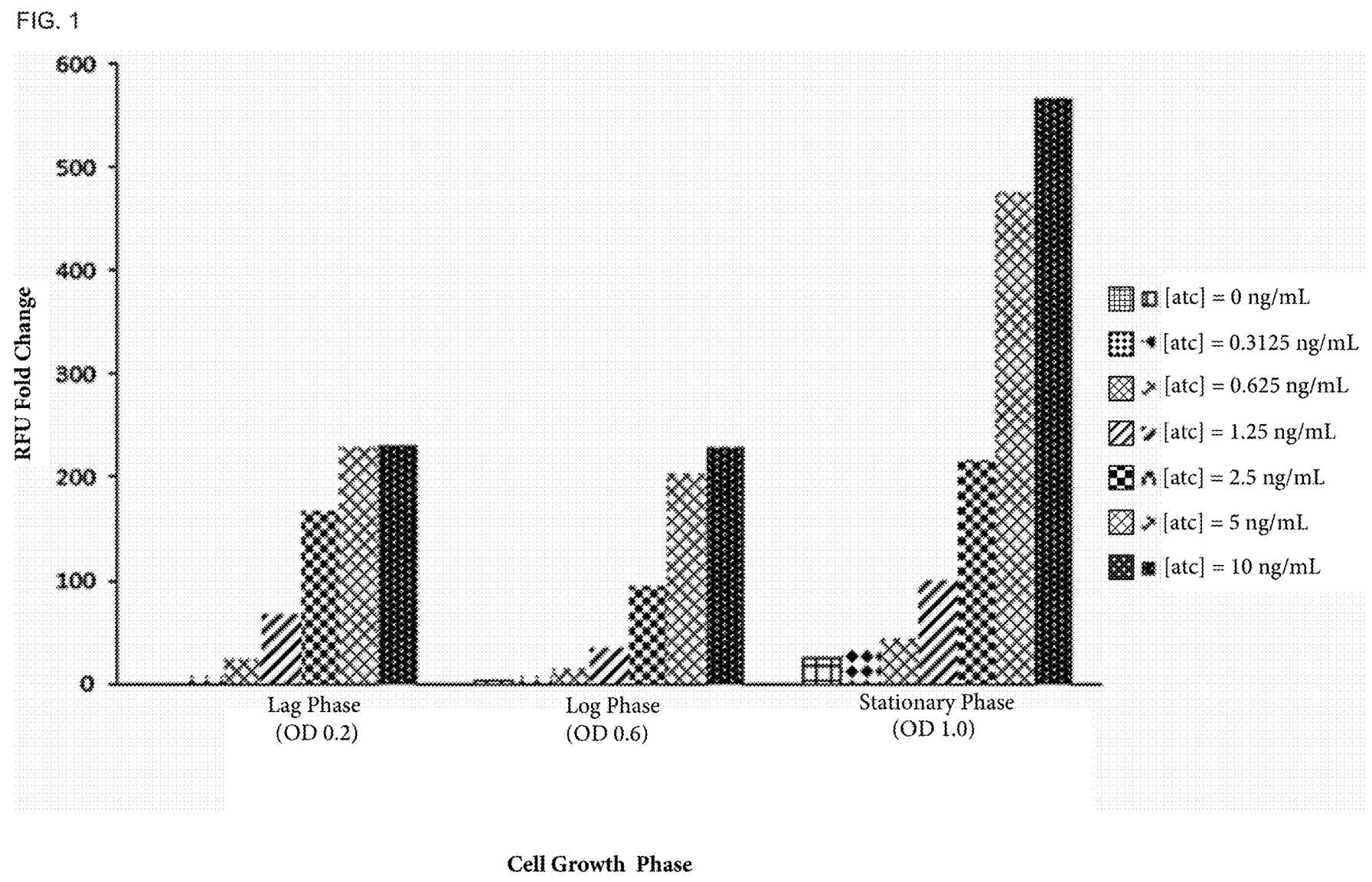

Legend:
- [atc] = 0 ng/mL
- [atc] = 0.3125 ng/mL
- [atc] = 0.625 ng/mL
- [atc] = 1.25 ng/mL
- [atc] = 2.5 ng/mL
- [atc] = 5 ng/mL
- [atc] = 10 ng/mL Y-axis: RFU Fold Change (0–600)
X-axis: Cell Growth Phase — Lag Phase (OD 0.2), Log Phase (OD 0.6), Stationary Phase (OD 1.0)

| | Wild-type slpA 5'UTR | Variant 1 5'UTR | Variant 2 5'UTR | Variant 3 5'UTR | Variant 4 5'UTR |
|---|---|---|---|---|---|
| mRNA structure | | | | | |
| Minimum free energy | -54.4 kcal/mol | -46.9 kcal/mol | -46.9 kcal/mol | -50.3 kcal/mol | -74.8 kcal/mol |
| Functional Consequences | - Stable hairpin<br>- Shielded 5' end<br>- Relaxed local binding at RBS | - Branched hairpin<br>- Exposed 5' end<br>- Tightened local binding at RBS | - Branched hairpin<br>- Shielded 5' end<br>- Relaxed local binding at RBS | - Destabilized hairpin<br>- Exposed 5' end<br>- Tightened local binding at RBS | - Tightened hairpin<br>- Shielded 5' end<br>- Relaxed local binding at RBS |

SEQUENCE LISTING

<160> NUMBER OF SEQ ID NOS: 27

<210> SEQ ID NO 1
<211> LENGTH: 703
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ttataaaaag atgttgacag cttgttctga tgatgataaa ctttaatagt tgcgagagaa      60
agaggagaaa tactagatga tgtctagatt agataaaagt aaagtgatta acagcgcatt     120
agagctgctt aatgaggtcg gaatcgaagg tttaacaacc cgtaaactcg cccagaagct     180
aggtgtagag cagcctacat tgtattggca tgtaaaaaat aagcgggctt tgctcgacgc     240
cttagccatt gagatgttag ataggcacca tactcacttt tgcccttag aaggggaaag      300 ctggcaagat ttttacgta ataacgctaa aagtttaga tgtgctttac taagtcatcg       360
cgatggagca aaagtacatt taggtacacg gcctacagaa aaacagtatg aaactctcga     420
aaatcaatta gcctttttat gccaacaagg ttttcacta gagaatgcat tatatgcact      480
cagcgctgtg gggcatttta ctttaggttg cgtattggaa gatcaagagc atcaagtcgc     540
taaagaagaa agggaaacac ctactactga tagtatgccg ccattattac gacaagctat     600
cgaattattt gatcaccaag gtgcagagcc agccttctta ttcggccttg aattgatcat     660
atgcggatta gaaaaacaac ttaaatgtga aagtgggtct taa                       703
```

<210> SEQ ID NO 2
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
tgcttgtggg ggtaagcggt aggtgaaata ttacaaatag tattttttcgg tcattttaac        60
ttgctatttc ttgaagaggt tagtacaata tgaatcgtgg ccctatcagt gatagagatc       120
aggcgcccta tcagtgatag agatgattct tcagcaagac tactacctca tgagagttat       180
agactcatgg atcttgcttt gaagggtttt gtacattata ggctcctatc acatgctgaa       240
cctatggcct attacatttt tttatatttc aaggaggaaa agaccac                     287
```

<210> SEQ ID NO 3
<211> LENGTH: 938
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
cccttctac ataccccct ttacacctac tccacctcta tattccatcc tgcttgtggg         60
ggtaagcggt aggtgaaata ttacaaatag tattttttcgg tcattttaac ttgctatttc     120
ttgaagaggt tagtacaata tgaatcgtgg taagtaatag gacgtgcttc aggcgtgttg     180
cctgtacgca tgctgattct tcagcaagac tactacctca tgagagttat agactcatgg     240
tataggctcc tatcacatgc tgaacctatg gcctattaca ttttttttata tttcaaggag     300
gaaaagacca catgatgtct agattagata aagtaaagt gattaacagc gcattagagc      360
tgcttaatga ggtcggaatc gaaggtttaa caacccgtaa actcgcccag aagctaggtg     420
tagagcagcc tacattgtat tggcatgtaa aaaataagcg ggctttgctc gacgccttag     480
ccattgagat gttagatagg caccatactc acttttgccc tttagaaggg gaaagctggc    540
aagatttttt acgtaataac gctaaaagtt ttagatgtgc tttactaagt catcgcgatg    600
gagcaaaagt acatttaggt acacggccta cagaaaaaca gtatgaaact ctcgaaaatc    660
aattagcctt tttatgccaa caaggttttt cactagagaa tgcattatat gcactcagcg     720
ctgtggggca ttttactta ggttgcgtat tggaagatca agagcatcaa gtcgctaaag    780
aagaaaggga acacctact actgatagta tgccgccatt attacgacaa gctatcgaat      840
tatttgatca ccaaggtgca gagccagcct tcttattcgg ccttgaattg atcatatgcg     900
gattagaaaa acaacttaaa tgtgaaagtg ggtcttaa                             938
```

<210> SEQ ID NO 4
<211> LENGTH: 191
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gtggtaagta ataggacgtg cttcaggcgt gttgcctgta cgcatgctga ttcttcagca        60
agactactac ctcatgagag ttatagactc atggatcttg ctttgaaggg ttttgtacat      120
tataggctcc tatcacatgc tgaacctatg gcctattaca ttttttttata tttcaaggag     180
gaaaagacca c                                                           191
```

<210> SEQ ID NO 5
<211> LENGTH: 627
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 5

```
atgatgtcac gcttggataa atcaaaagtt attaattcag cattggaatt gttgaatgaa      60
gttggcattg aaggcttgac cacccgcaaa ttggcacaaa aatttgggcgt tgaacaacca    120
accttgtatt ggcatgttaa aaataaacgc gcattgttgg atgcattggc aattgaaatg    180
ttggatcgcc atcataccca ttttttgccca ttggaaggcg aatcatggca agatttttg     240
cgcaataatg caaaatcatt tcgctgcgca ttgttgtcac atcgcgatgg cgcaaaagtt    300
catttgggca cccgcccaac cgaaaaacaa tatgaaacct ggaaaatca attggcattt     360
ttgtgccaac aaggcttttc attggaaaat gcattgtatg cattgtcagc agttggccat    420
tttaccttgg gctgcgtttt ggaagatcaa gaacatcaag ttgcaaaaga gaacgcgaa     480
accccaacca ccgattcaat gccaccattg ttgcgccaag caattgaatt gtttgatcat    540
caaggcgcag aaccagcatt tttgtttggc ttggaattga ttatttgcgg cttggaaaaa    600
caattgaaat gcgaatcagg ctcataa                                         627
```

<210> SEQ ID NO 6
<211> LENGTH: 693
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
cttaaaatat agtcatagaa ttagggcgtc ggttttaaaa gtgtggtaaa ataatggtca      60
agattaatga tgtctagatt agataaaagt aaagtgatta acagcgcatt agagctgctt    120
aatgaggtcg gaatcgaagg tttaacaacc cgtaaactcg cccagaagct aggtgtagag    180
cagcctacat tgtattggca tgtaaaaaat aagcgggctt tgctcgacgc cttagccatt    240
gagatgttag ataggcacca tactcacttt tgccctttag aaggggaaag ctggcaagat    300
ttttttacgta ataacgctaa aagttttaga tgtgctttac taagtcatcg cgatggagca    360
aaagtacatt taggtacacg gcctacagaa aaacagtatg aaactctcga aaatcaatta    420
gcctttttat gccaacaagg ttttttcacta gagaatgcat tatatgcact cagcgctgtg    480
gggcatttta ctttaggttg cgtattggaa gatcaagagc atcaagtcgc taaagaagaa    540
agggaaacac ctactactga tagtatgccg ccattattac gacaagctat cgaattattt    600
gatcaccaag gtgcagagcc agccttctta ttcggccttg aattgatcat atgcggatta    660
gaaaaacaac ttaaatgtga agtgggtct taa                                   693
```

<210> SEQ ID NO 7
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
cttaaaatat agtcatagaa ttagggcgtc ggttttaaaa gtgtggtaaa ataatggtca      60
agattagtgg taagtaatag gacgtgcttc aggcgtgttg cctgtacgca tgctgattct    120
```

```
tcagcaagac tactacctca tgagagttat agactcatgg tataggctcc tatcacatgc    180
tgaacctatg gcctattaca tttttttata tttcaaggag gaaaagacca catgatgtca    240
cgcttggata aatcaaaagt tattaattca gcattggaat tgttgaatga agttggcatt    300
gaaggcttga ccacccgcaa attggcacaa aaattgggcg ttgaacaacc aaccttgtat    360
tggcatgtta aaataaaacg cgcattgttg gatgcattgg caattgaaat gttggatcgc    420
catcataccc attttgccc attggaaggc gaatcatggc aagattttt gcgcaataat    480 gcaaaatcat ttcgctgcgc attgttgtca catcgcgatg gcgcaaaagt tcatttgggc    540
acccgcccaa ccgaaaaaca atatgaaacc ttggaaaatc aattggcatt tttgtgccaa    600
caaggctttt cattggaaaa tgcattgtat gcattgtcag cagttggcca ttttaccttg    660
ggctgcgttt tggaagatca agaacatcaa gttgcaaaag aagaacgcga aaccccaacc    720
accgattcaa tgccaccatt gttgcgccaa gcaattgaat tgtttgatca tcaaggcgca    780
gaaccagcat ttttgtttgg cttggaattg attatttgcg gcttggaaaa acaattgaaa    840
tgcgaatcag gctcataa                                                  858

<210> SEQ ID NO 8
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tgcttgtggg ggtaagcggt aggtgaaata ttacaaatag tatttttcgg tcattttaac     60
ttgctatttc ttgaagaggt tagtacaata tgaatcgtgg tccctatcag tgatagagat    120
caggcgccct atcagtgata gagatgattc ttcagcaaga ctactacctc atgagagtta    180
tagactcatg gatcttgctt tgaagggttt tgtacattat aggctcctat cacatgctga    240
acctatggcc tattacattt ttttatattt caaggaggaa aagaccac                 288

<210> SEQ ID NO 9
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
tgcttgtggg ggtaagcggt aggtgaaata ttacaaatag tatttttcgg tcattttaac     60
ttgctatttc ttgaagaggt tagtacaata tgaatcgtgg ccctatcagt gatagagatc    120
aggctcccta tcagtgatag agatgattct tcagcaagac tactacctca tgagagttat    180
agactcatgg atcttgcttt gaagggtttt gtacattata ggctcctatc acatgctgaa    240
cctatggcct attacatttt tttatatttc aaggaggaaa agaccac                  287

<210> SEQ ID NO 10
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

| | | |
|---|---|---|
| tgcttgtggg ggtaagcggt aggtgaaata ttacaaatag tattttcgg tcattttaac | 60 | |
| ttgctatttc ttgaagaggt tagtacaata tgaatcgtgg tccctatcag tgatagagat | 120 | |
| caggctccct atcagtgata gagatgattc ttcagcaaga ctactacctc atgagagtta | 180 | |
| tagactcatg gatcttgctt tgaagggttt tgtacattat aggctcctat cacatgctga | 240 | |
| acctatggcc tattacattt ttttatattt caaggaggaa aagaccac | 288 | |

<210> SEQ ID NO 11
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | |
|---|---|---|
| tgcttgtggg ggtaagcggt aggtgaaata ttacaaatag tattttcgg tcattttaac | 60 | |
| ttgctatttc ttgaagaggt tagtacaata tgaatcgtgg ccctatcagt gatagagata | 120 | |
| ggcgccctat cagtgataga gatgattctt cagcaagact actacctcat gagagttata | 180 | |
| gactcatgga tcttgctttg aagggttttg tacattatag ctcctatcat gctgaac | 240 | |
| ctatggccta ttcattttt ttatatttca aggaggaaaa gaccac | 286 | |

<210> SEQ ID NO 12
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

| | | |
|---|---|---|
| tgcttgtggg ggtaagcggt aggtgaaata ttacaaatag tattttcgg tcattttaac | 60 | |
| ttgctatttc ttgaagaggt tagtacaata tgaatcgtgg ccctatcagt gatagagatc | 120 | |
| aggcgcccta tcagtgatag agatattctt cagcaagact actacctcat gagagttata | 180 | |
| gactcatgga tcttgctttg aagggttttg tacattatag ctcctatcat gctgaac | 240 | |
| ctatggccta ttcattttt ttatatttca aggaggaaaa gaccac | 286 | |

<210> SEQ ID NO 13
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | | |
|---|---|---|
| tgcttgtggg ggtaagcggt aggtgaaata ttacaaatag tattttcgg tcattttaac | 60 | |
| ttgctatttc ttgaagaggt tagtacaata tgaatcgtgg ccctatcagt gatagagata | 120 | |
| ggcgccctat cagtgataga gatattcttc agcaagacta ctacctcatg agagttatag | 180 | |
| actcatggat cttgctttga agggttttgt acattatagg ctcctatcac atgctgaacc | 240 | |
| tatggcctat tacattttt tatatttcaa ggaggaaaag accac | 285 | |

<210> SEQ ID NO 14
<211> LENGTH: 287
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 14

```
tgcttgtggg ggtaagcggt aggtgaaata ttacaaatag tattttcgg tcatttaac    60
ttgctatttc ttgaagaggt tagtacaata tgaatcgtgg ccctatcagt gatagagatt  120
gacatcccta tcagtgatag agatgattct tcagcaagac tactacctca tgagagttat  180
agactcatgg atcttgcttt gaagggtttt gtacattata ggctcctatc acatgctgaa  240
cctatggcct attacatttt tttatatttc aaggaggaaa agaccac                287
```

<210> SEQ ID NO 15
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
tgcttgtggg ggtaagcggt aggtgaaata ttacaaatag tattttcgg tcatttaac    60
ttgctatttc ttgaagaggt tagtacaata tgaatcgtgg tccctatcag tgatagagat  120
tgacatccct atcagtgata gagatattct tcagcaagac tactacctca tgagagttat  180
agactcatgg atcttgcttt gaagggtttt gtacattata ggctcctatc acatgctgaa  240
cctatggcct attacatttt tttatatttc aaggaggaaa agaccac                287
```

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Ser
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Ala Ala Ala Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Ala Pro Ala Pro
1               5

```
<210> SEQ ID NO 19
<211> LENGTH: 44
<212> TYPE: DNA
<213> ORGANISM: Escherichia coli

<400> SEQUENCE: 19
ataaaacgaa aggctcagtc gaaagactgg gcctttcgtt ttat            44

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaatattaca aatagtattt ttcggtca                              28

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctctaacac tgttaggg                                         18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctgtatcac tgatacgg                                         18

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atcttgcttt gaagggtttt gtacat                                26

<210> SEQ ID NO 24
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tgcttgtggg ggtaagcggt aggtgaaata ttacaaatag tattttttcgg tcattttaac    60 ttgctaccct atcagtgata gagtacaata ccctatgagt gatagagaag gacgtgcttc   120
aggcgtgttg cctgtacgca tgctgattct tcagcaagac tactacctca tgagagttat   180
agactcatgg atcttgcttt gaagggtttt gtacattata ggctcctatc acatgctgaa   240
```

```
cctatggcct attacatttt tttatatttc aaggaggaaa agaccac            287
```

<210> SEQ ID NO 25
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
tgcttgtggg ggtaagcggt aggtgaaata ttacaaatag tattttttcgg tcattttaac    60 ttgctatttc ttgaagaggt tagtacaata tgaatcgtgg ccctatcagt gatagagatc   120
aggcgcccta tcagtgatag agatgattct tcagcaagac tactacctca tgagagttat   180
agactcatgg atcttgcttt gaagggtttt gtacattata ggctcctatc acatgctgaa   240
cctatggcct attacatttt tttatatttc aaggaggaaa agaccac                287
```

<210> SEQ ID NO 26
<211> LENGTH: 265
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
ccctatcagt gatagagata tttttcggtc attttaactt gctatttctt gaagaggtta    60
gtacaatatg aatcgtggta agtaatagga cgtgcttcag gcgtgttgcc tgtacgcatg   120
ctgattcttc agcaagacta ctacctcatg agagttatag actcatggat cttgctttga   180
agggttttgt acattatagg ctcctatcac atgctgaacc tatggcctac cctatcagtg   240
atagagacaa ggaggaaaag accac                                        265
```

<210> SEQ ID NO 27
<211> LENGTH: 262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
tgcttgtggg ggtaagcggt aggtgaaata ttacaaatag tattttttcgg tcattttaac    60 ttgctatttc ttgaagaggt tagtacaata tgaatcgtgg taaccctatc agtgatagag   120
attcttcacc ctatcagtga tagagagaga gttatagact catggatctt gctttgaagg   180
gttttgttct ctatcactga tagggacatg cttctctatc actgataggg attttttttat   240 atttcaagga ggaaaagacc ac                                           262
```

METHOD OF REGULATING GENE EXPRESSION IN A CELL

RELATED APPLICATIONS

This application is a National Stage Application under 35 U.S.C. 371 of PCT application PCT/US2018/025154 designating the United States and filed Mar. 29, 2018; which claims the benefit of U.S. provisional application No. 62/478,219 filed on Mar. 29, 2017 each of which are hereby incorporated by reference in their entireties.

STATEMENT OF GOVERNMENT INTERESTS

This invention was made with government support under DE-FG02-02ER63445 awarded by Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Mar. 29, 2018, is named 010498_01066_WO_SL.txt and is 15,441 bytes in size.

FIELD

The present invention relates in general to methods of regulating gene expression in a cell.

BACKGROUND

*Lactobacilli* are important industrial microbes in the dairy industry and are heavily targeted for use in vivo due to their FDA status as a generally regarded as safe (GRAS) probiotic organism. However, few genetic tools exist to control gene expression in *Lactobacilli*. Inducible expression systems are usually based on "borrowing" native regulation responsive to their cognate sugar activators. While several inducible promoters have been tried in *Lactobacilli*, all suffer from high levels of basal leakage because the rich media formulations required for the growth of most species already contain non-trivial levels of the inducing sugar. See T. Duong et al. Construction of vectors for inducible and constitutive gene expression in *Lactobacillus*. *Microb Biotech.* 2010 Jul; 4(3):357-67 and S. Heiss et al. Evaluation of novel inducible promoter/repressor systems for recombinant protein expression. *Microb Cell Fact.* 2016 March; 15(50) each of which are hereby incorporated by reference in its entirety.

Induction systems that have been used are the nisin-controlled gene expression (NICE) system and to a lesser extent the pSIP system, which use nisin and sakacin as inducing agents, respectively (see I. Mierau & M. Kleerebezem. 10 years of the nisin-controlled gene expression system (NICE) in *Lactococcus lactis. Appl Microbiol Biotcchnol.* 2005 July; 68(6):705-17 and E. Sorvig et at High-level, inducible gene expression in *Lactobacilus sakes* and *Lactobacillus plantarum* using versatile expression vectors. *Microbiology.* 2005 151:2439-49 each of which is hereby incorporated by reference in its entirety. While these systems have been used successfully in a variety of lactic acid bacteria in the past decade, they are unwieldy and inefficient. The NICE system, for example, requires its regulatory proteins to be encoded in the chromosome for proper function due to strict requirements of copy control. Since genome integration is a highly-inefficient process in well-studied *Lactobacilli* (see J. P. van Pijkeren & R. A. Britton. Precision genome engineering in lactic acid bacteria. *Microb Cell Fact.* 2014 August; 13(1):S10 hereby incorporated by reference in its entirety), and unavailable in most other strains, the NICE system cannot be easily used (see S. Pavan et al. Adaptation of the nisin-controlled expression system in Lactobacillus plantarum: a tool to study in vivo biological effects. *Appl Environ Microbiol.* 2000 66:4427-32 and Wu C M, Lin C F, Chang Y C, Chung R C. Construction and characterization of nisin-controlled expression vectors for use in *Lactobacillus reuteri. Biosci Biotechnol Biochem.* 2006 70:757-67 each of which are hereby incorporated by reference in its entirety). Furthermore, both nisin and sakacin are bacteriocins, and their antibiotic effects may be deleterious to the host species. There is a continuing need for methods and expression systems with improved control for gene expression.

SUMMARY

The present disclosure provides an inducible system for control of nucleic acid expression, such as gene expression, in lactic acid bacteria based on the use of an agent (i.e., binding agent or cognate binding agent) to bind to a transcription repressor protein in a manner to allow a constitutive promoter to begin transcription of a target nucleic acid or to otherwise control an otherwise constitutive promoter's activity insofar as the binding of the transcription repressor protein prevents transcription using the promoter and the binding of the agent to the transcription repressor protein allows transcription by the promoter. According to one aspect, a lactic acid bacterial cell includes a constitutive promoter sequence that has been altered to include one or more transcription repressor protein binding sites. The altered constitutive promoter sequence is operable when the one or more transcription repressor protein binding sites are unbound by a corresponding transcription repressor protein. According to one aspect, insertion of the one or more transcription repressor protein binding sites does not alter or significantly alter the ability of the constitutive promoter sequence to operate or function. Accordingly, transcription by the cell of the target nucleic acid sequence proceeds. When a transcription repressor protein is provided to the cell, such as by expression of a foreign nucleic acid sequence encoding for the corresponding transcription repressor protein, the transcription repressor protein binds to the transcription repressor protein binding site and transcription of the target nucleic acid sequence is repressed. According to one aspect, the transcription repressor protein may be allosteric. When a cognate binding agent is introduced to the cell, the binding agent binds to the transcription repressor protein causing an allosteric change which removes the transcription repressor protein from the transcription repressor protein binding site or otherwise prevents or inhibits binding of the transcription repressor protein to the transcription repressor protein binding site. As a result, transcription of the target nucleic acid sequence is activated. The nucleic acid sequence within the cell that includes the promoter sequence and the one or more transcription repressor binding sites may be referred to as an agent-responsive element to the extent that the altered promoter sequence (when the transcription repressor protein is bound to the transcription repressor protein binding site) is responsive to the binding agent, i.e., transcription is activated.

According to one exemplary embodiment, lactic acid bacteria are genetically modified to include a tetracycline-responsive element operably linked to a target nucleic acid sequence, such that the tetracycline-responsive element is inducible in the presence of tetracycline to initiate transcription of the target nucleic acid sequence into a corresponding mRNA and translation into a corresponding amino acid sequence. Methods of making lactic acid bacterial cells including an inducible system for control of gene expression based on agent-responsive promoters or elements, such as tetracycline-responsive promoters, genetic constructs and the use of such cells are also disclosed.

According to one aspect, a method is provided for controlling the expression of one or more proteins by a lactic acid bacterial cell within a subject including introducing into the subject a lactic acid bacterial cell or population of lactic acid bacterial cells including (1) an endogenous constitutive promoter sequence modified to include one or more transcriptional repressor protein binding sites, wherein the promoter sequence is operably linked to one or more target nucleic acid sequences encoding the one or more proteins; and (2) exogenous nucleic acid sequence encoding one or more transcriptional repressor proteins corresponding to the one or more transcriptional repressor protein binding sites, wherein the one or more transcriptional repressor proteins, when expressed, bind to the one or more transcriptional repressor protein binding sites to repress transcription of the target nucleic acid sequence, and providing the subject with a cognate binding agent which binds to the one or more transcriptional repressor proteins to activate the promoter and induce transcription of the one or more target nucleic acid sequences.

Further features and advantages of certain embodiments of the present invention will become more fully apparent in the following description of embodiments and drawings thereof, and from the claims.

BRIEF DESCRIPTION OF THE DRAWINGS

FIG. 1 depicts the results of repression and expression of a fluorescent protein in the absence and presence of aTc in *L. rhamnosus* GG.

FIG. 8 depicts the nucleic acid sequence design for Variant 2 (SEQ ID NO: 25).

FIG. 11 depicts in schematic minimum free energy mRNA structural folding predictions for various mRNA structures.

DETAILED DESCRIPTION

Figure 2:
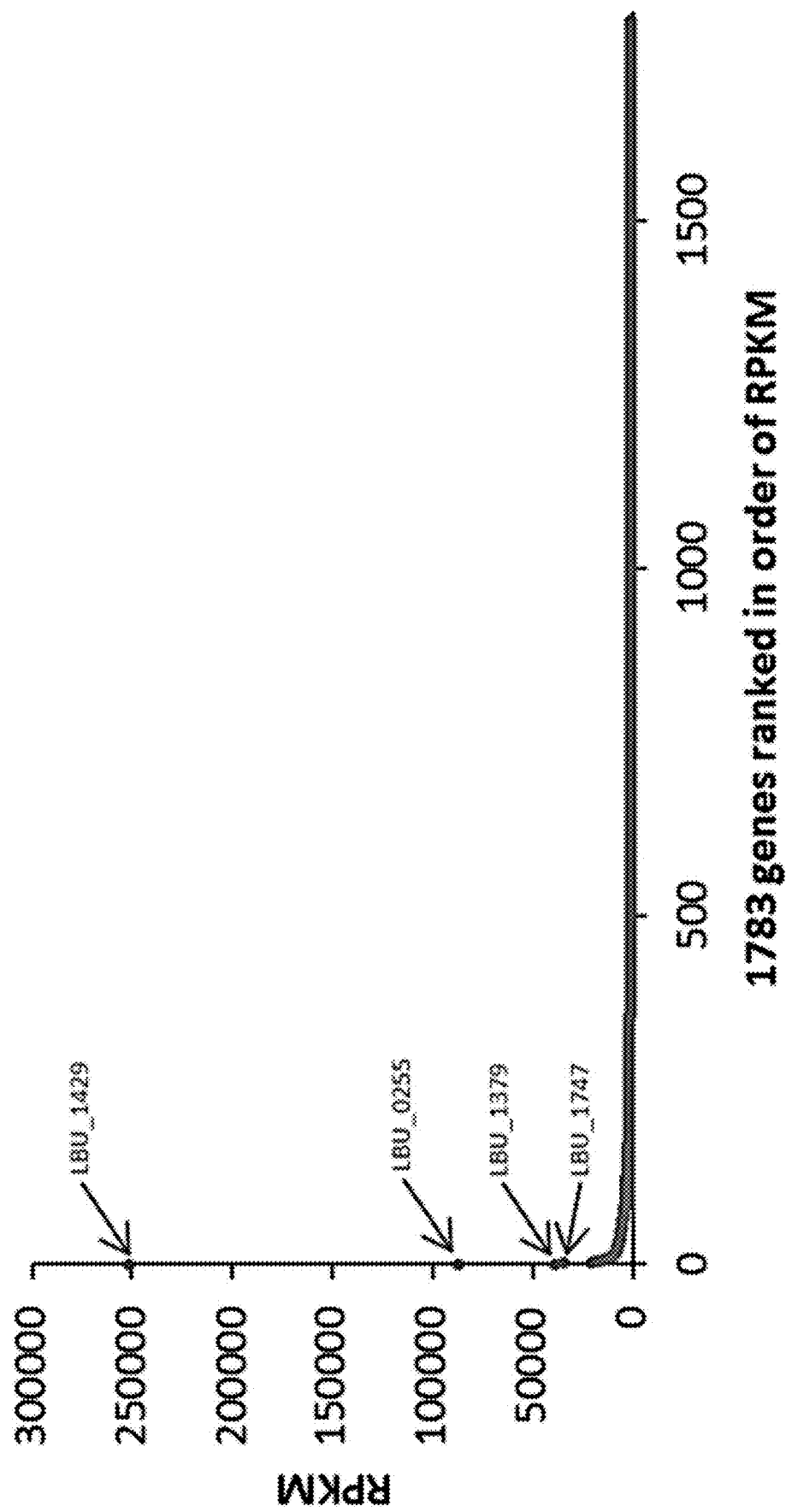
FIG. 2 depicts data of gene expression of *L. delbrueckii* 2038.

The practice of certain embodiments or features of certain embodiments may employ, unless otherwise indicated, conventional techniques of molecular biology, microbiology, recombinant DNA, and so forth which are within ordinary skill in the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Terms and symbols of nucleic acid chemistry, biochemistry, genetics, and molecular biology used herein follow those of standard treatises and texts in the field, e.g., Kornberg and Baker, *DNA Replication*, Second Edition (W. H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in its entirety.

It is to be understood that embodiments of the present disclosure are intended to utilize the particular sequences disclosed herein and sequences having at least 85% homology, at least 90% homology, at least 95% homology, at least 97% homology, at least 98% homology or at least 99% homology to the particular sequence disclosed herein.

The present disclosure provides a lactic acid bacterial cell including a first exogenous nucleic acid sequence comprising an agent-responsive element operably linked to a target nucleic acid sequence, such that the agent-responsive element is inducible in the presence of the agent to initiate transcription of the target nucleic acid sequence into a corresponding mRNA and translation into a corresponding amino acid sequence. According to one aspect, the agent bonds to a transcriptional repressor protein which may or may not be bound to a transcriptional repressor protein binding site to cause an allosteric or conformational change to the transcriptional repressor protein thereby releasing the transcriptional repressor protein from the transcriptional repressor protein binding site or thereby preventing binding of the transcriptional repressor protein to the transcriptional repressor protein binding site, thereby allowing transcription of the target nucleic acid sequence.

According to one aspect, the agent-responsive element includes a constitutive promoter sequence modified to include one or more exogenous transcriptional repressor protein binding sites corresponding to one or more transcriptional repressor proteins, wherein the constitutive promoter sequence within the agent-responsive element is operable to initiate transcription of the target nucleic acid sequence in the absence of one or more transcriptional repressor proteins.

According to one aspect, the agent-responsive element includes a constitutive promoter sequence modified to include one or more exogenous transcriptional repressor protein binding sites and wherein the lactic acid bacterial cell further includes an exogenous nucleic acid sequence encoding one or more transcriptional repressor proteins corresponding to the one or more transcriptional repressor protein binding sites, wherein the one or more transcriptional repressor proteins, when expressed, bind to the one or more transcriptional repressor protein binding sites to repress transcription of the target nucleic acid sequence, and wherein, the agent activates the promoter, i.e. agent-responsive promoter or element, and induces transcription of the target nucleic acid sequence.

Aspects of the present disclosure include the genetic modification of a cell to include foreign genetic material which can then be expressed by the cell. The cell may be modified to include any other genetic material or elements useful in the expression of a nucleic acid sequence. Foreign genetic elements may be introduced or provided to a cell using methods known to those of skill in the art. A genetically modified cell encompasses lactic acid bacterial cells that have been engineered to include an episomal or expression vector or otherwise incorporate a nucleic acid sequence, such as for example in the genome or the cell. Cells and techniques for cellular transformation are well known in the art (see e.g., Sambrook, et al., Molecular Cloning: A Laboratory Manual, 2nd ed., Cold Spring Harbor (1989)).

Embodiments of the present disclosure provide a genetically modified lactic acid bacterial cell including a first nucleic acid sequence comprising a first promoter operably linked to a DNA binding molecule such as a tetracycline repressor gene coding sequence, and a second nucleic acid sequence comprising a second promoter operably linked to a target nucleic acid sequence such as a coding sequence of a gene of interest wherein the second promoter is modified to include one or more DNA binding molecule binding sites, such as tetracycline repressor protein binding sites.

Embodiments of the present disclosure are directed to methods of making a tetracycline inducible expression system in a lactic acid bacterial cell. The cell is genetically modified to include a first nucleic acid sequence comprising a first promoter operably linked to a tetracycline repressor gene coding sequence, and a second nucleic acid sequence comprising a second promoter operably linked to a coding sequence of a gene of interest wherein the second promoter is modified to include one or more tetracycline repressor protein binding sites. The first promoter drives constitutive expression of a tetracycline repressor. The second promoter regulates the expression of a gene of interest in response to tetracycline induction.

Embodiments of the present disclosure provide for a first nucleic acid sequence including a first promoter operably linked to a tetracycline repressor gene coding sequence. The first promoter can be any promoter that is operable in a lactic acid bacterial cell. Preferably, the first promoter can drive constitutive expression of the tet repressor. In an exemplary embodiment, the first nucleic acid sequence is represented by a sequence having at least 85% homology, at least 90% homology, at least 95% homology, at least 97% homology, at least 98% homology or at least 99% homology to SEQ ID NO: 1 and the first promoter is an *L. plantarum* ribosomal RNA promoter.

Embodiments of the present disclosure provide for a second nucleic acid sequence including a second promoter operably linked to a coding sequence of a gene of interest wherein the promoter is modified to include one or more tetracycline repressor protein binding sites. The second promoter is inducible by an inducing agent. In an exemplary embodiment, the promoter is inducible by tetracycline or its analogs or functional equivalents. The second promoter is operable in lactic acid bacterial cells. In an exemplary embodiment, the second promoter is an slpA promoter. The second promoter is modified to include one or more tetracycline repressor protein binding sites so that tight control of gene expression in the respective prokaryotic or eukaryotic cell can be achieved. In one embodiment, the modified promoter sequence has at least 85% homology, at least 90% homology, at least 95% homology, at least 97% homology, at least 98% homology or at least 99% homology to SEQ ID NO: 2 or SEQ ID NO: 4.

Embodiments of the present disclosure provide an expression vector including a nucleic acid sequence including a promoter operably linked to a coding sequence of a gene of interest wherein the promoter is modified to include one or more tetracycline repressor protein binding sites. Further, a polynucleotide sequence can be operably linked to the promoter. The polynucleotide sequence may be a polynucleotide sequence encoding a gene, an antisense polynucleotide, a ribozyme, a fusion protein, a polynucleotide encoding an antibody, or therapeutic protein etc.

Lactic Acid Bacterial Cells

Cells according to the present disclosure include lactic acid bacterial cells. Exemplary lactic acid bacterial cells include bacterial cells within the order Lactobacillales. According to one aspect, bacterial cells include bacterial cells from the genus *Lactobacillus, Leuconostoc, Pediococcus, Lactococcus, Streptococcus, Carnobacterium, Enterococcus, Oenococcus, Tetragenococcus, Vagococcus,* or *Wei-*

*sella.* According to one aspect, bacterial cells include bacterial cells from the species *Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus alvei, Lactobacillus alvi, Lactobacillus amylolyticus, Lactobacillus amylophilus, Lactobacillus amylotrophicus, Lactobacillus amylovorus, Lactobacillus animalis, Lactobacillus animata, Lactobacillus antri, Lactobacillus apinorum, Lactobacillus apis, Lactobacillus apodemi, Lactobacillus aquaticus, Lactobacillus aviarius, Lactobacillus backii, Lactobacillus bifermentans, Lactobacillus bombi, Lactobacillus bombicola, Lactobacillus brantae, Lactobacillus brevis, Lactobacillus brevisimilis, Lactobacillus buchneri, Lactobacillus cacaonum, Lactobacillus camelliae, Lactobacillus capillatus, Lactobacillus casei, Lactobacillus paracasei, Lactobacillus zeae, Lactobacillus catenefornis, Lactobacillus ceti, Lactobacillus coleohominis, Lactobacillus colini, Lactobacillus collinoides, Lactobacillus composti, Lactobacillus concavus, Lactobacillus coryniformis, Lactobacillus crispatus, Lactobacillus crustorum, Lactobacillus curieae, Lactobacillus curvatus, Lactobacillus delbrueckii, Lactobacillus dextrinicus, Lactobacillus diolivorans, Lactobacillus equi, Lactobacillus equicursoris, Lactobacillus equigenerosi, Lactobacillus fabifermentans, Lactobacillus faecis, Lactobacillus faeni, Lactobacillus farciminis, Lactobacillus farraginis, Lactobacillus fermentum, Lactobacillus floricola, Lactobacillus florum, Lactobacillus formosensis, Lactobacillus fornicalis, Lactobacillus fructivorans, Lactobacillus frumenti, Lactobacillus fuchuensis, Lactobacillus furfuricola, Lactobacillus futsaii, Lactobacillus gallinarum, Lactobacillus gasseri, Lactobacillus gastricus, Lactobacillus ghanensis, Lactobacillus gigeriorum, Lactobacillus ginsenosidimutans, Lactobacillus gorillae, Lactobacillus graminis, Lactobacillus guizhouensis, Lactobacillus halophilus, Lactobacillus hammesii, Lactobacillus hamsteri, Lactobacillus harbinensis, Lactobacillus hayakitensis, Lactobacillus heilongjiangensis, Lactobacillus helsingborgensis, Lactobacillus helveticus, Lactobacillus herbarum, Lactobacillus heterohiochii, Lactobacillus hilgardii, Lactobacillus hokkaidonensis, Lactobacillus hominis, Lactobacillus homohiochii, Lactobacillus hordei, Lactobacillus iatae, Lactobacillus iners, Lactobacillus ingluviei, Lactobacillus insectis, Lactobacillus insicii, Lactobacillus intermedius, Lactobacillus intestinalis, Lactobacillus iwatensis, Lactobacillus ixorae, Lactobacillus japonicus, Lactobacillus jensenii, Lactobacillus johnsonii, Lactobacillus kalixensis, Lactobacillus kefiranofaciens, Lactobacillus kefiri, Lactobacillus kimbladii, Lactobacillus kimchicus, Lactobacillus kimchiensis, Lactobacillus kisonensis, Lactobacillus kitasatonis, Lactobacillus koreensis, Lactobacillus kullabergensis, Lactobacillus kunkeei, Lactobacillus larvae, Lactobacillus leichmannii, Lactobacillus letivazi, Lactobacillus lindneri, Lactobacillus malefermentans, Lactobacillus mali, Lactobacillus manihotivorans, Lactobacillus mellifer, Lactobacillus mellis, Lactobacillus melliventris, Lactobacillus micheneri, Lactobacillus mindensis, Lactobacillus mixtipabuli, Lactobacillus mobilis, Lactobacillus modestisalitolerans, Lactobacillus mucosae, Lactobacillus mudanjiangensis, Lactobacillus murinus, Lactobacillus nagelii, Lactobacillus namurensis, Lactobacillus nantensis, Lactobacillus nasuensis, Lactobacillus nenjiangensis, Lactobacillus nodensis, Lactobacillus odoratitofui, Lactobacillus oeni, Lactobacillus oligofermentans, Lactobacillus ori, Lactobacillus oryzae, Lactobacillus otakiensis, Lactobacillus ozensis, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pasteurii, Lactobacillus paucivorans, Lactobacillus pentosus, Lactobacillus perolens, Lactobacillus plajomi, Lactobacillus plantarum, Lactobacillus pobuzihii, Lactobacillus pontis, Lactobacillus porcinae, Lactobacillus psittaci, Lactobacillus rapi, Lactobacillus rennanquilfy, Lactobacillus rennini, Lactobacillus reuteri, Lactobacillus rhamnosus, Lactobacillus rodentium, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus saniviri, Lactobacillus satsumensis, Lactobacillus secaliphilus, Lactobacillus selangorensis, Lactobacillus senioris, Lactobacillus senmaizukei, Lactobacillus sharpeae, Lactobacillus shenzhenensis, Lactobacillus sicerae, Lactobacillus silagei, Lactobacillus siliginis, Lactobacillus similis, Lactobacillus songhuajiangensis, Lactobacillus spicheri, Lactobacillus sucicola, Lactobacillus suebicus, Lactobacillus sunkii, Lactobacillus taiwanensis, Lactobacillus thailandensis, Lactobacillus tucceti, Lactobacillus ultunensis, Lactobacillus uvarum, Lactobacillus vaccinostercus, Lactobacillus vaginalis, Lactobacillus vermiforme, Lactobacillus vespulae, Lactobacillus vini, Lactobacillus wasatchensis, Lactobacillus xiangfangensis, Lactobacillus yonginensis,* or *Lactobacillus zymae.*

Cells according to the present disclosure include any lactic acid bacterial cell such as those listed at world wide website ncbi.nlm nih.gov/Taxonomy/Browser/wwwtax.cgi?id=1578 into which nucleic acids having modified or altered promoter sequences operably linked to a target nucleic acid sequence of interest, such as a gene, can be introduced and expression of the gene of interest can be regulated by an inducing agent as described herein. It is to be understood that the basic concepts of the present disclosure described herein are not limited by cell type.

Another aspect of the invention pertains to host cells into which a recombinant expression vector of the invention has been introduced. The recombinant expression vector may include the agent-responsive promoter or element as described herein. The recombinant expression vector may include the nucleic acid encoding the transcriptional repression protein. The recombinant expression vector may include the altered or modified promoter sequence that includes one or more transcriptional repression protein binding sites. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Agent-Responsive Element

According to one aspect, the disclosure provides an agent-responsive element. The agent responsive element includes one or more of a constitutive promoter sequence, which may be endogenous or exogenous, and one or more exogenous transcriptional repressor protein binding sites corresponding to one or more transcriptional repressor proteins. The constitutive promoter sequences may be modified or altered to include the one or more exogenous transcriptional repressor protein binding sites corresponding to one or more transcriptional repressor proteins. The constitutive promoter sequence combined with one or more exogenous transcriptional repressor protein binding sites is operable to initiate transcription of the target nucleic acid sequence in the absence of one or more transcriptional repressor proteins. According to one aspect, the presence of the one or more exogenous transcriptional repressor protein binding sites may not inhibit the transcription of a target nucleic acid sequence as activated by the constitutive promoter sequence. The one or more exogenous transcriptional repressor protein binding sites may be placed upstream of the constitutive promoter sequence or within the constitutive promoter sequence. The agent, as described herein, is an entity that binds to the transcriptional repressor protein in a manner to inhibit binding of the transcriptional repressor protein to the transcriptional repressor protein binding site. When binding of the transcriptional repressor protein to the transcriptional repressor protein binding site is inhibited, transcription of the target nucleic acid sequence is promoted or activated through the constitutive promoter.

According to one aspect, a constitutive promoter sequence is modified to include one or more transcriptional repressor protein binding sites. The promoter sequence may be referred to as an altered promoter sequence or a modified promoter sequence. The transcriptional repressor protein binding site has a corresponding transcriptional repressor protein that binds to the transcriptional repressor protein binding site. The transcriptional repressor protein has a cognate binding partner that when bound to the transcriptional repressor protein inhibits binding of the transcriptional repressor protein to the transcriptional repressor protein binding site by way of allosteric change of the transcriptional repressor protein or steric hindrance or other mechanism of inhibition. An exemplary agent-induction system is the tetracycline induction system which has been used extensively in bacterial, fungal, plant, and mammalian systems. See J. L. Ramos et al. The TetR family of transcriptional repressors. *Microbiol Mol Biol Rev,* 2005 June; 69(2):326-56; E. Gari et al. A set of vectors with a tetracycline-regulatable promoter system for modulated gene expression in *Saccharomyces cerevisiae. Yeast.* 1997 July; 13(9):837-48; P. Weinmann et al. A chimeric transactivator allowes tetracycline-responsive gene expression in whole plants. *Plant J.* 1994 April; 5(4):559-69 and M. Gossen & H. Bujard. Tight control of gene expression in mammalian cells by tetracycline-responsive promoters. PNAS, 1992 Jun. 15; 89(12):5547-51 each of which are hereby incorporated by reference in its entirety. According to certain aspects, a tetracycline-regulatable promoter system, with tetracycline being the agent that induces transcription, is exemplary because of its ability to facilitate tight regulation and exhibit superior dynamic range of up to 5000-fold (see R. Lutz & H. Bujard. Independent and tight regulation of transcriptional units in *Escheria coli* via the LacR/O, the TetR/O and AraC/I1-I2 regulatory elements hereby incorporated by reference in its entirety), as well as its orthogonality to host factors. According to one aspect, the agent-responsive element and the agent are exemplary in their ability to exhibit, in most hosts of interest, little to no crosstalk between the system and host genetics or metabolism. Heterologous gene expression may thus be more reliably controlled by the experimenter. A tetracycline-regulatable promoter system is particularly exemplary. This feature of a tetracycline-regulatable promoter system also enables tetracycline or anhydrous tetracycline (aTc) induction's use in vivo. See X. Xia et al. In vitro- and in vivo-induced transgene expression in human embryonic stem cells and derivatives. *Stem Cells.* 2008 December; 26(2):525-33 and L. E. Dow et al. inducible in vivo genome editing with CR1SPR-Cas9. *Nat Biotech.* February 18; 33:390-4 each of which are hereby incorporated by reference in its entirety. Cas proteins are found in *Streptococcus pyogenes, S. thermophiles, S. aureus* or any other strain known to those of skill in the art.

According to one aspect, the promoter is endogenous and is a strong constitutive promoter with a longer promoter sequence into which operator boxes may be placed to control and regulate the promoter, Longer promoter sequences allow operator boxes to be inserted and not abrogate promoter ability but also to stop promoter ability when the transcriptional repressor protein binds.

As used herein, the term "repressor" or "transcriptional repressor protein" refers to a molecule capable of inhibiting the expression of a particular nucleic acid sequence, such as a gene, from a promoter. In effect, the molecule "represses" the expression of the gene from its promoter. In general, repressor systems will readily be recognized by those of skill in the art based on the present disclosure and which include a DNA binding site also referred to as a transcriptional repressor protein binding site or operator sequence and its corresponding binding partner also referred to as a transcriptional repressor protein. When the DNA binding site is included into a DNA sequence in a cell and the corresponding binding partner is provided to the cell, the corresponding binding partner binds to the DNA binding site. Such a system can be used to inhibit transcription when operably linked to a promoter sequence. Such a system can be included into a constitutive promoter sequence to transform the constitutive promoter sequence into an inducible promoter sequence. According to this aspect, the binding of the corresponding binding partner to the DNA binding site within a promoter sequence inhibits transcription of a target nucleic acid sequence operatively connected or linked to the promoter sequence. When the corresponding binding partner is removed from the DNA binding site, the constitutive promoter sequence begins transcription of the target nucleic acid sequence.

According to one aspect, an agent is provided that binds to the transcriptional repressor protein causing a conformational change in the transcriptional repressor protein thereby rendering it unable to bind to the transcriptional repressor protein binding site. In this manner, the transcriptional repressor protein is allosteric insofar as it can change structure or form when bound by an agent. In this manner, repressor dimerization and function may be disrupted. An agent may also inhibit binding of the transcriptional repressor protein through steric hindrance or other methods.

Transcriptional repressor proteins and their cognate binding sites are known to those of skill in the art and such as the TetR/tetO system, LacR/lacO or TreR/treO (lactose and trehalose controlled repression). For example, the tet repressor (TetR) is a protein that represses gene transcription of the tet operon upon binding to its cognate tet operator sequences tetO (tet binding sites) within the operon promoter. One of skill will readily identify useful TetR sequences based on the present disclosure including those identified in Ramos et al., The TetR Family of Transcriptional Repressors, Microbiology and Molecular Biology Reviews, June 2005, P. 326-356 hereby incorporated by reference in its entirety.

The TetR/tetO system is said to be a tetracycline responsive system insofar as tetracycline, anhydrous tetracycline or suitable derivatives of tetracycline may prevent binding of the tetracycline repressor to the tet operator sequences. Additional agent-responsive promoter systems include metabolite responsive systems such as metabolite-controlled operator boxes paired with their corresponding repressor such as LacR/lacO & TreR/treO (lactose and trehalose controlled repression). Additional repressor systems exist which are based on binding agents such as glucose, mannose, fructose, galactose, sucrose, raffinose, maltose, arabinose, ribose, sorbose, rhamnose, xylose which inhibit binding of a cognate transcriptional repressor protein thereby activating traqnscription. Such repressor systems may be included within any promoter sequence, such as slpA.

According to certain aspects, a cell is genetically modified to include one or more exogenous nucleic acids encoding for a transcriptional repressor protein and wherein the cell includes the cognate transcriptional repressor protein binding site. A binding agent cognate to the transcriptional repressor protein is also provided. The cell may also be genetically modified to include one or more exogenous nucleic acid sequences including one or more transcriptional repressor protein binding sites. Transcriptional repressor proteins and their corresponding or cognate binding agents are known to those of skill in the art and include those listed in Table 1 below.

TABLE 1

| Transcriptional Repressor Protein | Binding Agent | Type of Transcriptional Repressor Protein |
|---|---|---|
| ttgR | naringennin (flavanoids) | Transcriptional repressor |
| mphR | macrolides | Transcriptional repressor |
| tetR | tetracycline, anhydrous tetracycline, tetracycline derivatives, tetracycline analogs | Transcriptional repressor |
| gntR | Gluconate | Transcriptional repressor |
| galS | Galactose | Transcriptional repressor |
| trpR | tryptophan | Transcriptional repressor |
| qacR | Berberine | Transcriptional repressor |
| rmrR | Phytoalexin | Transcriptional repressor |
| cymR | Cumate | Transcriptional repressor |
| varR | Virginiamycin | Transcriptional repressor |
| rhaR | Rhamnose | Transcriptional repressor |

It is to be understood that the examples of transcriptional repressors and their corresponding binding agents are exemplary only and that one of skill in the art can readily identify additional transcriptional repressors and their corresponding binding agents for use in the present disclosure. Aside from the TetR family of transcriptional repressors, any member of the main bacterial transcriptional repressor families could be similarly implemented. This list includes members of the ArgR, AsnC/LrP, DeoR, GalR/LacI, GntR, IclR, LysR, MerR, MetJ, ModE, PadR and XRE families, not excluding other groups or subgroups of transcriptional regulators from bacterial, phagic or mammalian origin directly used or repurposed for their application in Lactobacilli.

Transcriptional repressors and/or binding agents may be natural or synthetic. One of skill can also design synthetic transcriptional repressors to bind to natural or non-natural cognate nucleic acid sequences and which may further bind natural or non-natural binding agents using methods known to those of skill in the art. The transformed cell is intended to express the transcriptional repressor under suitable conditions. Methods described herein can be used to insert the nucleic acids into the genome of the cells that are responsible for production of transcriptional repressors.

According to one aspect, the transformed, recombinant cell expresses the transcriptional repressor protein which regulates production of a target nucleic acid, for example, by binding to transcriptional repressor protein binding site within a promoter thereby inhibiting transcription of the target nucleic acid. According to one aspect, when expressed, the transcriptional repressor protein prevents the cell from expressing the target nucleic acid, either by blocking the expression (i.e. a repressor) of the target nucleic acid unless the transcriptional repressor protein is bound by the binding agent, which leads to target nucleic acid expression. According to one aspect for an allosteric transcription factor that is a repressor, the repressor protein blocks transcription of the reporter gene by binding as an oligomer to a region of DNA 5' to the reporter gene unless the desired binding agent binds the repressor thereby disrupting the oligomeric behavior and thus frequently preventing the effective binding of the complex to its cognate operator sequences. According to a further aspect, the transformed, recombinant cell is provided with a binding agent which binds to the transcription repressor protein in a manner to promote production of the peptide, polypeptide or amino acid sequence corresponding to the target nucleic acid sequence. According to one aspect, in the absence of the binding agent, the transcription repressor protein prevents transcription of the target nucleic acid.

Target Nucleic Acid Sequence

Target nucleic acid sequences maybe of any sequences desired to be transcribed. Target nucleic acid sequences include those that encode for therapeutic proteins, diagnostic proteins, reporter proteins, genes or enzymes.

As used herein, "gene" refers to the nucleic acid sequence that undergoes transcription as the result of promoter activity. A gene may code for a particular protein or, alternatively, code for an RNA sequence that is of interest in itself, e.g. because it acts as an antisense inhibitor.

Therapeutic proteins envisioned herein include proteins, such as endogenous proteins, associated with probiotic function (e.g. LGG p40, spaC), antibodies (including IgG, IgE, IgA, scFv and camlid antibodies—that target infectious agents, or host cell-surface proteins and antibody Fc), antimicrobial peptides of mammalian, viral, and bacterial origin (e.g. collistin, caerin, dermaseptin, LL-37, HBD-2) antiviral peptides (e.g. HCV-C5A, Fuzeon), cytokines (e.g. IL-10), allergens (e.g. pollen, nut proteins), worm protein (e.g. hookworm protein), trefoil factor, dietary enzymes, mucin binding proteins (e.g. intJ, GroEL), invasins, antitoxins or any antigen derived from an infectious agent delivered as a vaccination target.

Diagnostic proteins envisioned herein include antibodies that also can be used as diagnostic sensors, reactive oxygen species sensors or temperature sensors.

According to one aspect, the target nucleic acid sequence or downstream gene is a detectable moiety or reporter, such as a fluorescent moiety, such as GFP, that can be detected by fluorimetry, for example. An exemplary detectable moiety is a reporter protein. Reporter proteins envisioned herein include fluorescent proteins, luminescent proteins, enzymatic reporters such as GusA or PepN. Aspects of the methods described herein may make use of epitope tags and reporter gene sequences as detectable moieties. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, maltose binding protein, luciferase, green fluorescent protein (GFP), HcRed, DsRed, cyan fluorescent protein (CFP), yellow fluorescent protein (YFP), and autofluorescent proteins including blue fluorescent protein (BFP). Exemplary fluorescent protein reporters are provided at world wide website tsienlab.ucsd.edu/Samples/Constructs.htm. Any aforementioned instance of reporter proteins may be conjoined, with or without a peptide linker (such as

[GGGS]$_n$ (SEQ ID NO: 16), G$_n$, [EAAAK]$_n$ (SEQ ID NO: 17), or PAPAP (SEQ ID NO: 18) where n is the number of motif repeats), to any of the aforementioned target nucleic acid sequences, thereby yielding a fusion protein with double function or function attributable to each portion or segment fused together.

Definitions

As used herein, the term "recombinant" refers to nucleic acid that is formed by experimentally recombining nucleic acid sequences and sequence elements. A recombinant host would be any host receiving a recombinant nucleic acid and the term "recombinant protein" refers to protein produced by such a host.

As used herein, the term "expression" refers to the process by which a polypeptide is produced from DNA. The process involves the transcription of the gene into mRNA and the translation of this mRNA into a polypeptide. Depending on the context in which it is used, the term "expression" may refer to the production of RNA, protein or both.

As used herein, the term "operably linked" refers to genetic elements that are joined in such a manner that enables them to carry out their normal functions. For example, a gene is operably linked to a promotor when its transcription is under the control of the promotor and such transcription produces the protein normally encoded by the gene.

Vectors

As used herein, the term "vector" refers to a nucleic acid sequence capable of transporting another nucleic acid to which it has been linked. In certain aspects of the invention, vectors and plasmids useful for transformation of a variety of host cells are provided. Vectors and plasmids are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.). Vectors used to deliver the nucleic acids to cells as described herein include vectors known to those of skill in the art and used for such purposes.

As used herein, the term "episomal or expression vector" or comparable terms refer to a vector which is capable of inducing the expression of a nucleic acid sequence encoding a gene that has been cloned into it after transformation into a cell. The cloned nucleic acid sequence is usually placed under the control of (i.e., operably linked to) certain regulatory sequences such as a promoter.

In certain exemplary embodiments, recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990) hereby incorporated by reference in its entirety. It will be appreciated by those skilled in the art that the design of the expression vector can depend on such factors as the choice of the host cell to be transformed, the level of expression of protein desired, and the like.

One type of vector is a "plasmid," which refers to a circular double stranded DNA loop into which additional DNA segments can be ligated. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, or YAC (yeast artificial chromosome) or any other suitable vector.

Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Viral vectors include those where additional DNA segments can be ligated into the viral genome, a bacteriophage or viral genome, or any other suitable vector. The host cells can be any cells in which the vector is able to replicate.

Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

Typically, the vector or plasmid contains sequences directing transcription and translation of a relevant gene or genes and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

According to certain aspect of the invention, phages and their genetic material are provided. As used herein, the terms "phage" and "bacteriophage" are used interchangeably. Phage can be distinguished from each another based on their genetic composition and/or their virion morphology. Some phage have double stranded DNA genomes, including phage of the Corticoviridae, Lipothrixviridae, Plasmaviridae, Myroviridae, Siphoviridae, Sulfolobus, Podoviridae, Tectiviridae and Fuselloviridae families. Other phage have single stranded DNA genomes, including phage of the Microviridae and Inoviridae families. Other phage have RNA genomes, including phage of the Leviviridae and Cystoviridae families. Exemplary bacteriophage include, but are not limited to, Wphi, Mu, T2, T2, T3, T4, T5, T6, T7, P1, P2, P4, P22, fd, phi6, phi29, phiC31, phi80, phiX174, SP01, M13, MS2, PM2, SSV-1, L5, PRD1, Qbeta, lambda, UC-1, HK97, HK022 and the like. Exemplary phages include *lactobacillus* phages such as those described in world wide website ncbi.nlm nih.gov/taxonomy/?term=*Lactobacillus*+phage, including Bacteriophage phiADH, which has been used to transform *L. gasseri* as described in Appl Environ Microbiol. 2010 June; 76(12): 3878-3885 hereby incorporated by reference in its entirety.

Embodiments of the present disclosure include the use of an inducible system as described herein in a plasmid as well as an entity integrated into the host cell genome, via plasmids with enzymatic elements that direct chromosomal integration of expression cassettes encoded on the plasmid or any kind of suicidal plasmids that leverage the recombination machinery of the cell for integration into its genome. Such vectors are described in Ortiz-Martin et al., J Microbiol Methods. 2006 December; 67(3):395-407. Epub 2006 Jun. 5 hereby incorporated by reference in its entirety and can be designed by those of skill in the art based on the present disclosure.

Promoter Sequences

According to methods and constructs described herein, promoter sequences may be constitutive, inducible or repressible. As used herein, the term "promotor" refers to a DNA sequence that initiates the transcription of a gene. Promoters are typically found 5' to the gene and located proximal to the start codon. If a promotor is of the inducible type (i.e., exemplary tetracycline inducible promoters of the present disclosure), then the rate of transcription increases in response to an inducing agent or binding agent, i.e. tetracycline. The promoter can be modified to include one or more transcription repressor protein binding sites, also referred to herein as operator sequences, to improve the regulatory functionality of the promoter in response to an inducing agent, such as tetracycline. It is to be understood that the driving promoter sequence for any endogenous protein can be used in the methods described herein. The driving promoter for any Lactobacillus phage protein can be used in the methods described herein. One of skill will have ready access to the identification of such promoter sequences of any host organism of interest. Exemplary host strains include *L. delbruckii, L. gasseri, and L. rhamnosus* GG) and other host strains as described herein. Exemplary promoter sequences include the slpA promoter sequence from *L. acidophilus*, the clpC promoter *L. fermentum* BR11, the lacA promoter from *L. lactis*, the ldh promoter from *L. plantarum, L. casei*, or *L. reuteri*, the pgm promoter from *L. agilis*, and the ermB promoter from *E. faecalis*. One of skill in the art will readily be able to identify cognates of these exemplary promoters in sister organisms, and other promoter sequences in addition to the slpA promoter sequence through analysis of sequence databases. Such databases include whole genome DNA sequences that can be mined for promoter elements, and transcriptome RNA sequences, that can be sorted by apparent expression strength through computation of the relative abundance via the quantification of transcripts (e.g., 'RPKM'). Highly expressive promoters can thus be predicted from RNA transcripts exhibiting high transcriptional counts. For example, previously published transcriptome data from *L. delbrueckii* (H Zheng et al. Strans-specific RNA-seq analysis of *Lactibacillus delbrueckii* subsp. *Bulgaricus transcriptome. Mol. Biosyst.*, 2016, 12, 508 hereby incorporated by reference in its entirety) can be analyzed by plotting the RPKM profile of this strain. See FIG. 2. This procedure highlights the highly expressed genes, LBU_1429, LBU_0225, LBU_1379, and LBU_1747, whose promoter sequences are exemplary based on the present disclosure.

Figure 3:
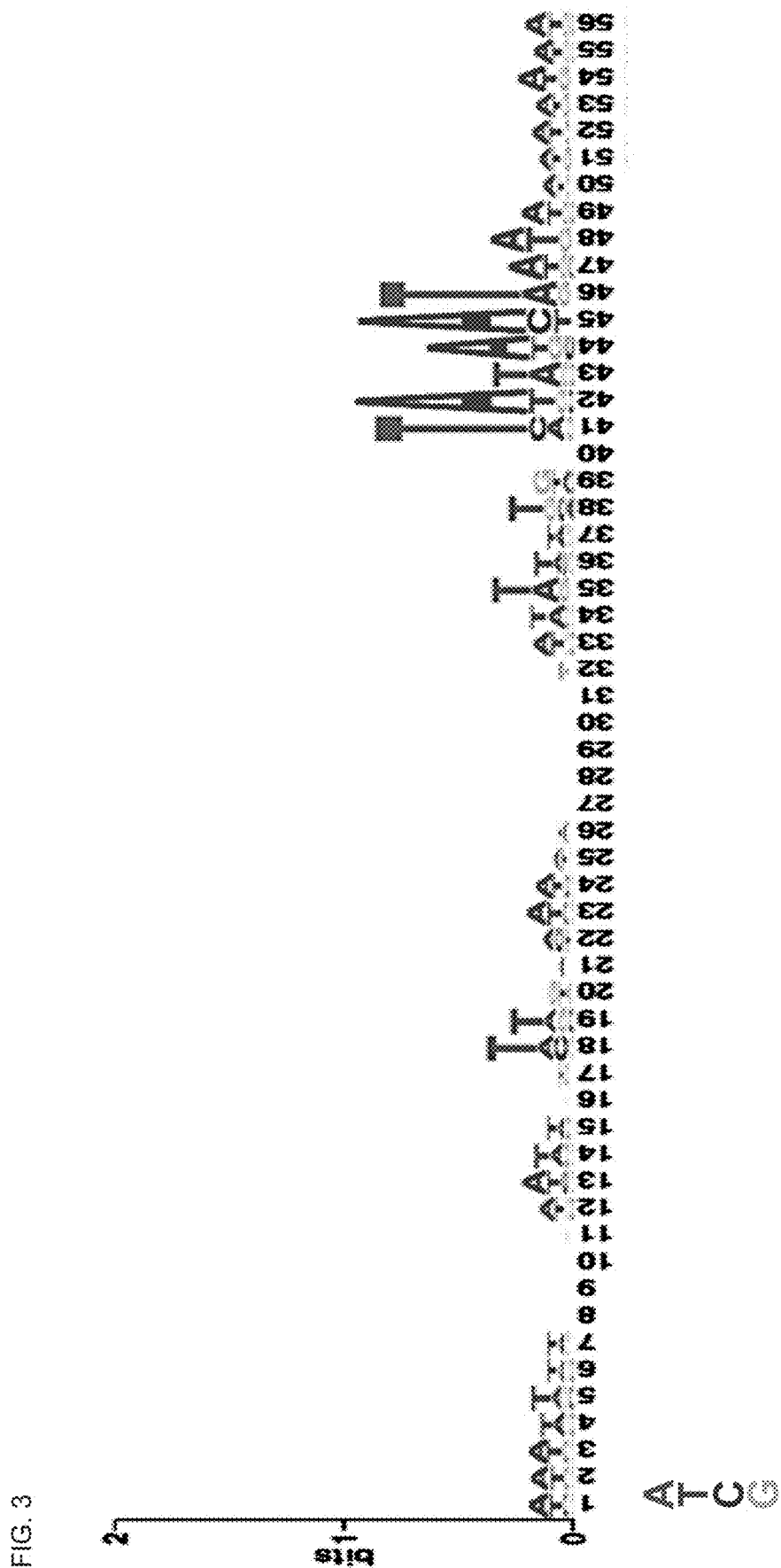
FIG. 3 is a graph depicting a consensus sequence generated from all sequenced *Lactobacillus delbruckii*.
Figure 4:
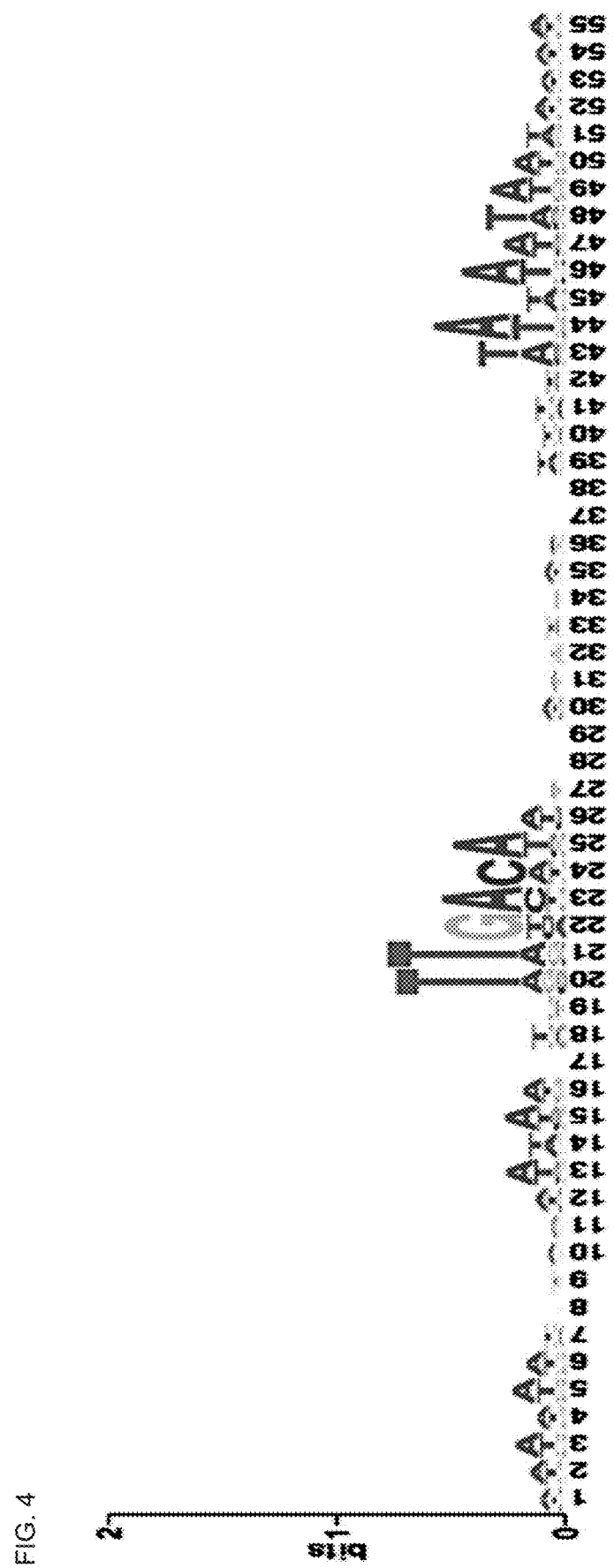
FIG. 4 is a graph depicting a consensus sequence generated from all sequenced *Lactobacillus rhamnosus* GG.
Figure 5:
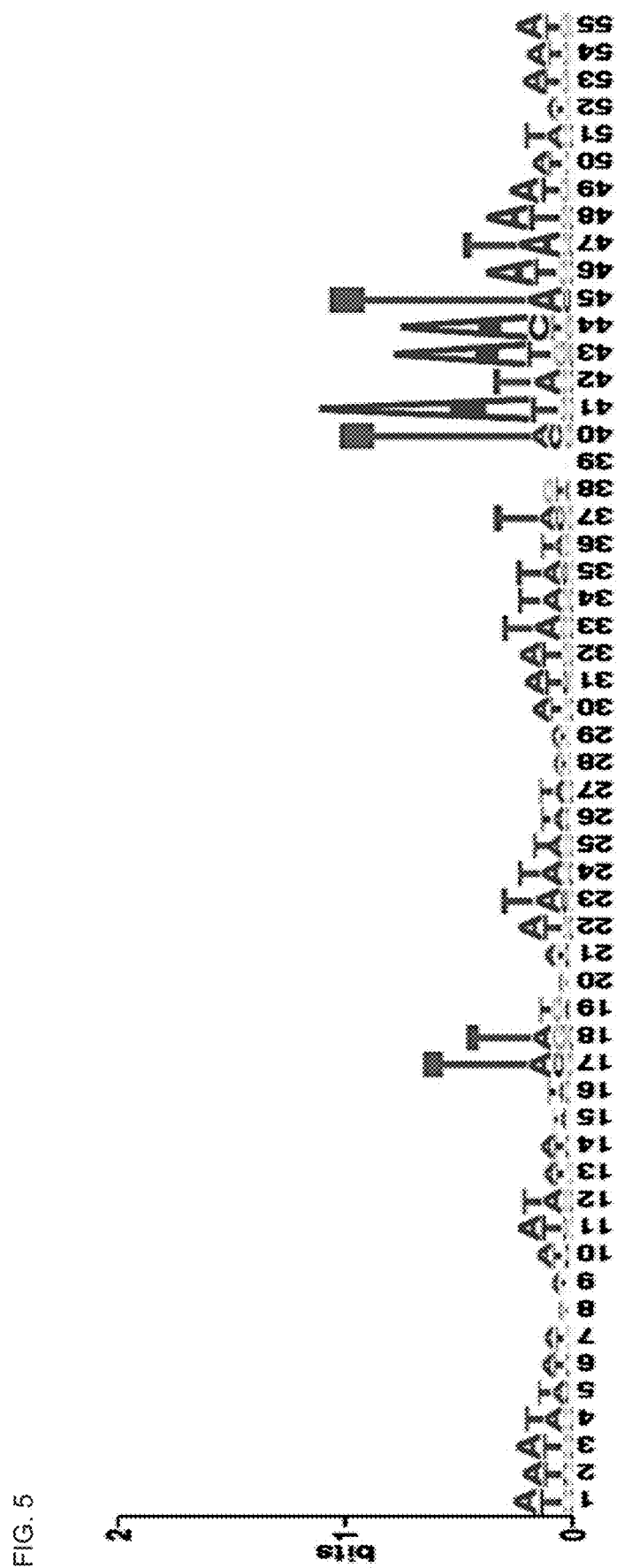
FIG. 5 is a graph depicting a consensus sequence generated from all sequenced *Lactobacillus gasseri*.
Figure 6:
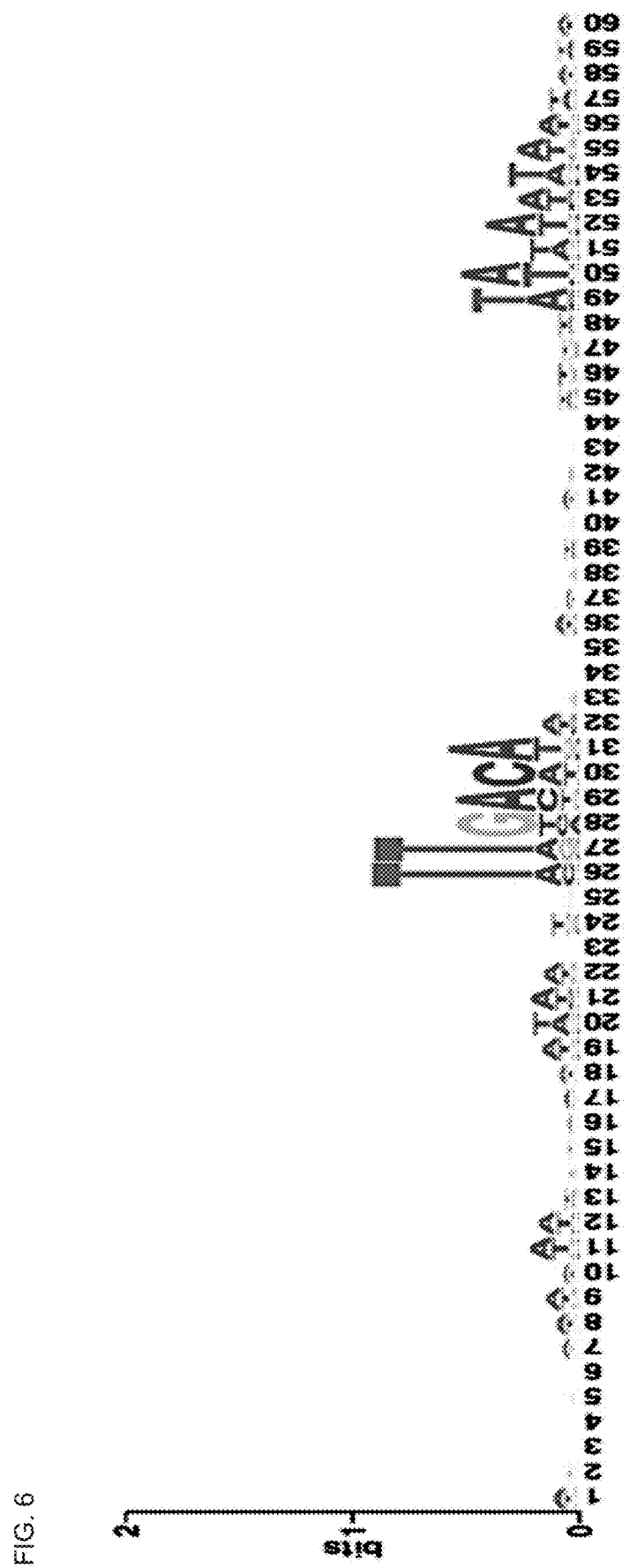
FIG. 6 is a graph depicting a consensus sequence generated from all sequenced *Lactobacillus* Phages.

According to one aspect, computational techniques known to those of skill in the art can be used to identify all predicted promoter sequences from all sequenced *Lactobacillus* phages. Particularly exemplary are *Lactobacillus* phages as most phage genes tend to be strongly expressed. Synthetically derived promoter sequences can also be used, i.e., computationally optimized sequences generated by identifying consensus sequences from known databases where every permutation of displayed bases can be strung together into a potential promoter and where blank positions can be filled with any of A, T, G, or C. Sequences with at least 80% sequence identity, at least 85% sequence identity, at least 90% sequence identity, at least 95% sequence identity, at least 97% sequence identity, at least 98% sequence identity, or at least 99% sequence identity with any of these resulting, synthetic promoter sequences have similar efficacy. FIG. 3 is a graph depicting a consensus sequence generated from all sequenced *Lactobacillus delbruckii*. FIG. 4 is a graph depicting a consensus sequence generated from all sequenced *Lactobacillus rhamnosus* GG. FIG. 5 is a graph depicting a consensus sequence generated from all sequenced *Lactobacillus gasseri*. FIG. 6 is a graph depicting a consensus sequence generated from all sequenced *Lactobacillus* Phages. These consensus sequences provide the relative frequencies of an A, T, G, or C occurring at each position of the consensus promoter sequence, which can be used to generate libraries of synthetic promoters that are theoretically optimized for robust expression in that host (in the case a strain-specific consensus as in FIGS. 4 and 5) or for *Lactobacilli* in general (in the case of a phage-derived consensus as in FIG. 6).

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA, orfX, and xylT promoters (useful for expression in Gram-positive bacteria, Eichenbaum et al. *Appl. Environ. Microbiol.* 64(8):2763-2769 (1998)); Sorvig et al. *FEMS Microbiol. Lett.* 229:119-126 (2003), Miyoshi et al., *FEMS Microbiol. Lett.* 239(2):205-212 (2004)); the lac, tre, FOS promoters (useful for expression in *Lactobacilli*, Duong et al. *Microb. Biotech*, 4(3):357-367 (2010)); ribosomal RNA subunit promoters and synthetic derivatives thereof such as the synthetic P11 promoter (useful for expression in *Lactobacillus plantarum*, Rud et al., Microbiology 152:1011-1019 (2006)). Termination control regions may also be derived from various genes native to the preferred hosts.

Regulatory elements are contemplated for use with the methods and constructs described herein. The term "regulatory element" is intended to include promoters, enhancers, internal ribosomal entry sites (IRES), and other expression control elements (e.g. catabolite repressive elements, transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein.

Terminators

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein. Rho-independent, hairpin-forming terminator sequences are of particular use in lactic acid bacteria, and effective terminators include, but are not limited to, the rrnB T1 terminator sequence:

```
                                      (SEQ ID NO: 19)
ATAAAACGAAAGGCTCAGTCGAAAGACTGGGCCTTTCGTTTTAT.
```

Genetic Modification

Foreign nucleic acids (i.e., those which are not part of a cell's natural nucleic acid composition) may be introduced into a cell using any method known to those skilled in the art for such introduction. Such methods include transfection, transformation, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Methods and materials of non-viral delivery of nucleic acids to cells further include biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE I

Methods of Making a Tetracycline Inducible Expression System in *Lactobacilli*

The present disclosure provides a TetR-PltetO system using different promoters than are featured in the original TetR-PltetO system, so as to function in lactic acid bacteria. In general, the TetR-PltetO system drives the expression of the gene encoding the efflux pump TetA (which provides antibiotic resistance against tetracycline in bacteria). TetR is a transcriptional repressor that prevents the transcription of the tetA gene from the PltetO promoter in absence of tetracycline, by means of attaching to the so-called tetO operator boxes (the TetR binding sites). In the presence of the antibiotic, TetR disengages from PltetO, allowing access by RNA polymerase and thus permitting the transcription of the resistance gene tetA. This way, the transmembrane efflux pump is produced only when needed.

An expression system that is inducible by tetracycline in *Lactobacilli* is described as follows. It was first verified that

*Lactobacilli* possess no resistance genes that would adulterate any induction system based on the addition of tetracycline or any of its analogs. A BLAST analysis of the TetR protein sequence as well as the TetA tetracycline efflux pump that drives resistance was performed, across all available *Lactobacillus* proteomes and potential homologs in *L. lactis*, and *L. plantarum* were identified, because they carry a transferrable plasmid harboring tetM and tetS genes. These plasmids can be eliminated from these strains with novobiocin so that this system can still be implemented in them, but regardless, no other strain of *Lactobacillus* possessed any sequences pertinent to tetracycline. This was imperically validated by testing several strains (*L. rhamnosus* GG, *L. gasseri, L. jensenii*, and *L. crispatus*) for their susceptibility to tetracycline, and found their growth to be inhibited with as little as 2 mg/mL of tetracycline, indicating a lack of any resistance mechanism in these strains.

Existing formats of tetracycline responsive promoters, such as those frequently utilized in the PltetO system in *E. coli*, do not function in *Lactobacilli*. This is because the architecture of promoters in *Lactobacilli* differ from that in *E. coli*, i.e. the average separation between the −35 and −10 boxes recognized by the $\sigma^{70}$ subunit of the RNA polymerase is 17 bp as opposed to 16 bp, and the sequence space in this region requires more AT-rich content in *Lactobacilli*. The length of this spacing sequence is related to the recognizing of the −35 and −10 boxes by $\sigma^{70}$ as consensus boxes can render very poor gene expression if they are too far apart or too close. Additionally, *Lactobacillus* promoters frequently contain AT-rich upstream promoter elements that can interact with α or σ factors and are thus important for robust expression. Therefore, to design a functional tetracycline response promoter for use in *Lactobacilli*, the promoter sequence that drives the expression of the s-layer protein A (slpA) in *L. acidophilus* is manipulated in a manner to operably link it to tetracycline. This promoter exhibits strong, robust expression of heterologous protein in diverse species of *Lactobacilli*, making it an exemplary design template (A. McCracken et al. Analysis of promoter sequences from *Lactobacillus* and *Lactococcus* and their activity in several *Lactobacillus* species. Arch Microbiol. 2000 173:383-389).

To edit the slpA promoter sequence in order to bring it under the control of tetracycline, the tetO operator box sequence from the PltetO system was inserted into various regions within the promoter sequence. lacO and treO—the operator box sequences for trehalose and lactose based repression identified in the native Plac and Ptre promoters in *L. acidophilus* (see Duong et al. *Microb. Biotech,* 4(3):357-367 (2010) hereby incorporated by reference in its entirety) were inserted into the region upstream to slpA, replacing a segment of the original sequence (preserving the original length of the operator box) at the same relative locations as they are in the wild-type, trehalose and lactose inducible promoters where the operator boxes were first characterized. Doing so resulted in Lactose and Trehalose driven induction of slpA, exceeding the performances of the original promoters. The strategy was replicated for tetracycline and various variants were tested as follows.

Figure 7:
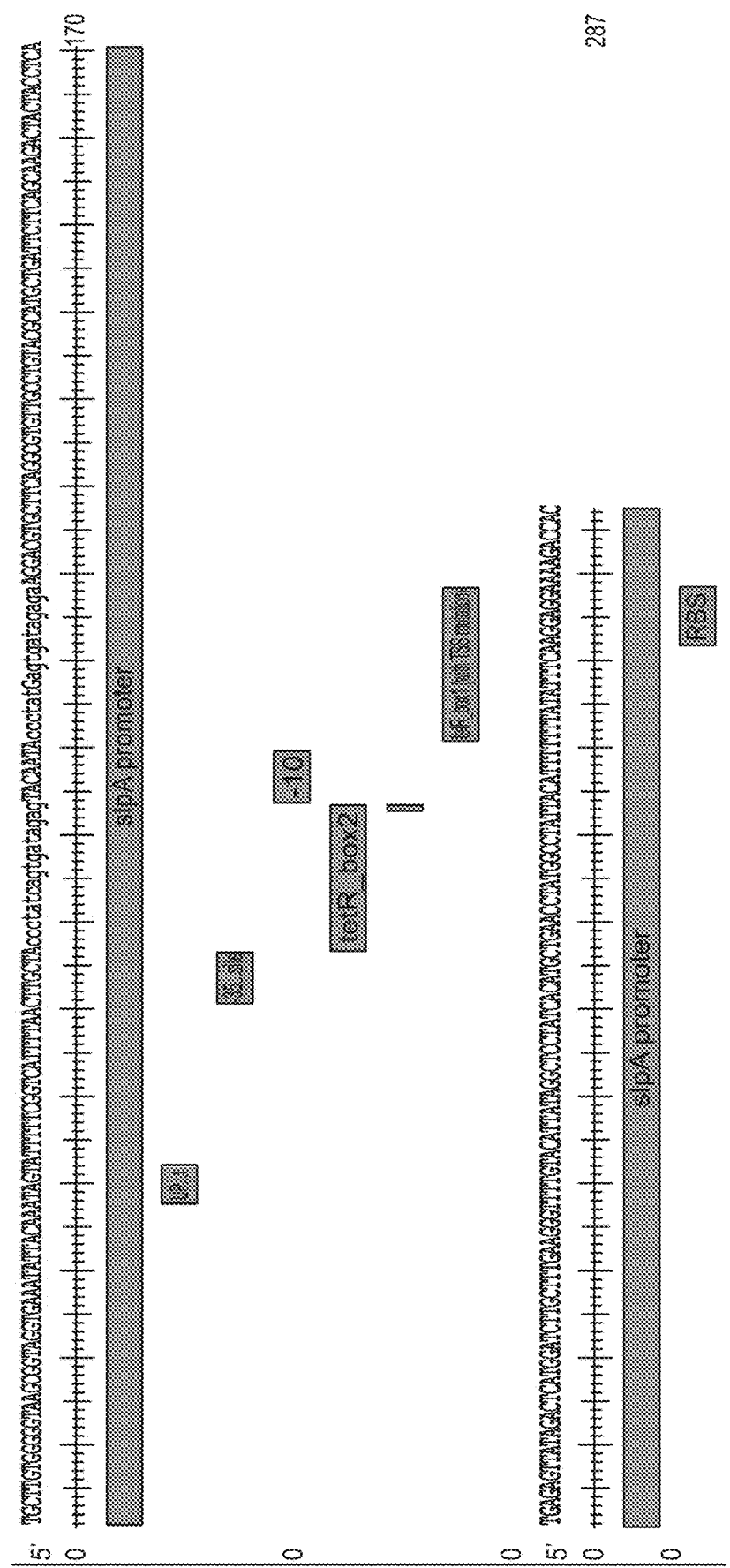
FIG. 7 depicts the nucleic acid sequence design for Variant 1 (SEQ ID NO: 24).

Variant 1: The relative locations of the tetR operators were preserved as they exist in the *E. coli* PltetO expression system. However, a single base pair substitution was made within the tetO box downstream of the −10 sequence, in order to preserve the base encoding for the transcriptional start site (TSS) for slpA, as the tetO placement overlaps with that position (i.e., the C in the 7th base of the tetO sequences was mutated to a G) as shown in FIG. 7.

Figure 8:
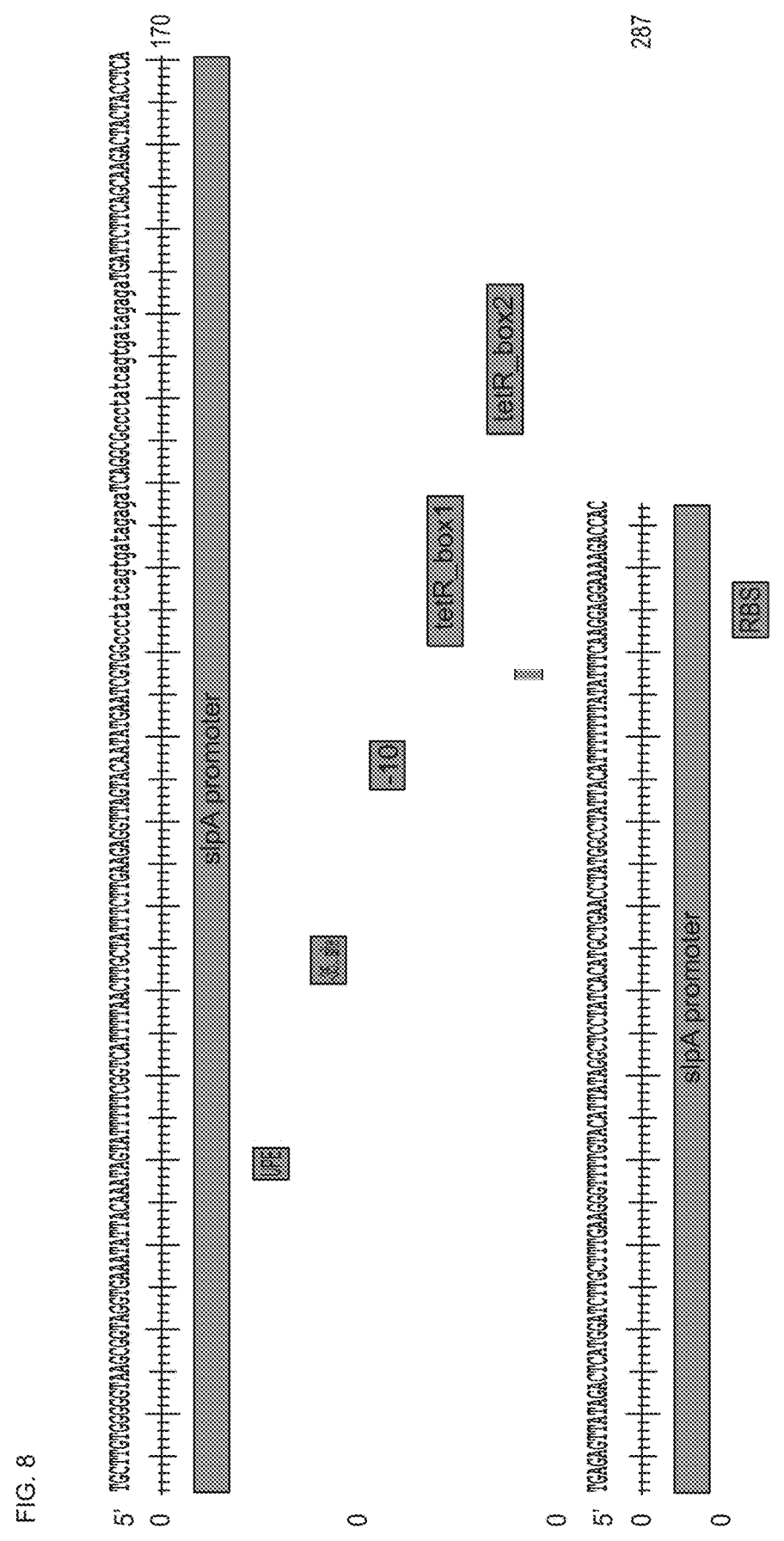

Variant 2: In this variant, the tetO boxes were inserted in locations that minimally perturb the −35/−10, and upstream promoter sequence region. They are placed subsequent to the transcriptional start site, so that TetR protein binding physically restricts processing by RNA polymerase, rather than preventing RNA polymerase binding in the first place (as is encoded by the tetO placement in Variant 1). See FIG. 8.

Figure 9:
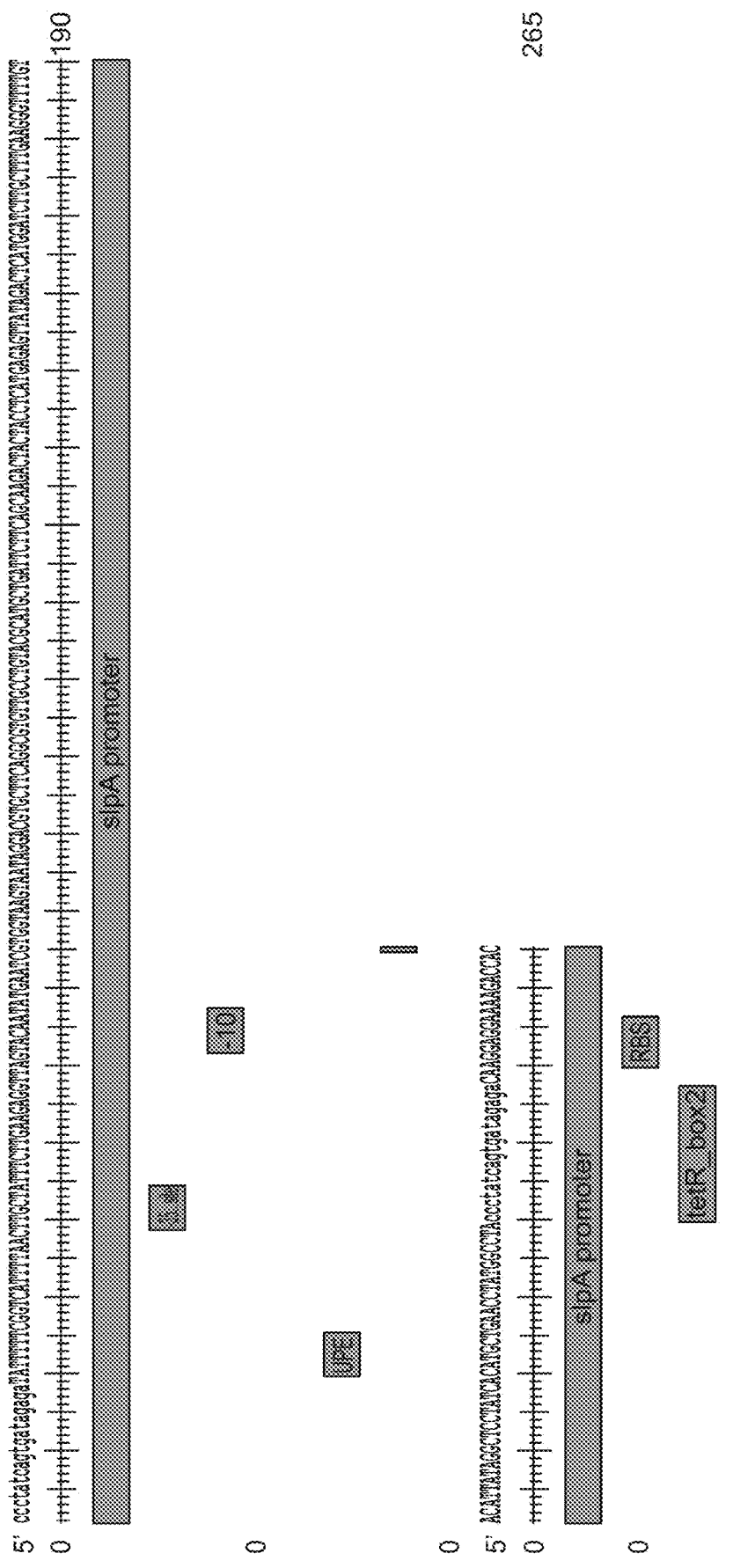
FIG. 9 depicts the nucleic acid sequence design for Variant 3 (SEQ ID NO: 26).

Variant 3: This design mimics the relative placement of operator boxes common to carbohydrate linked induction such as lactose and trehalose. The tetO boxes are placed 5' to the "upstream promoter element" and 5' to the RBS. See FIG. 9.

Figure 10:
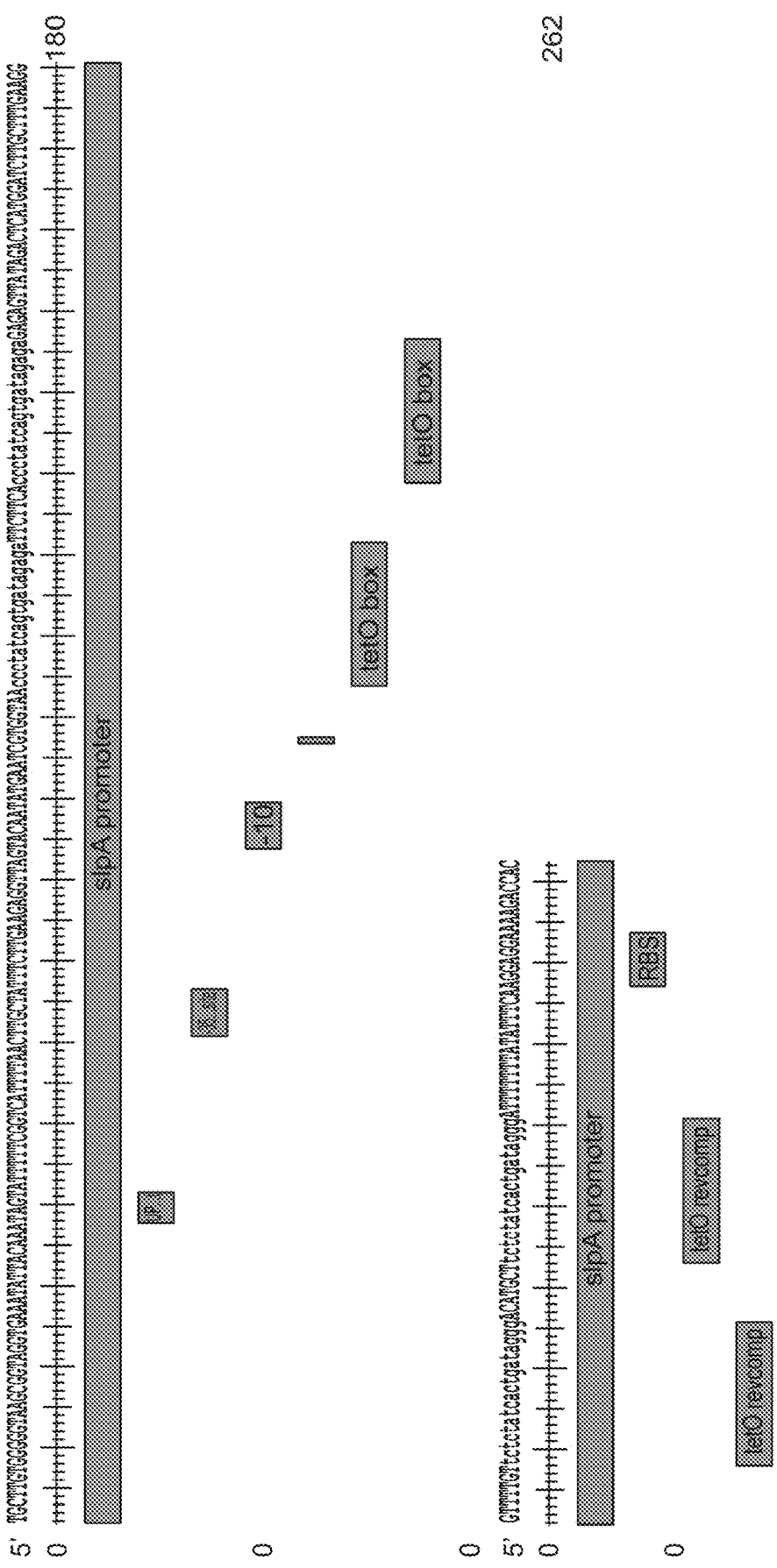
FIG. 10 depicts the nucleic acid sequence design for Variant 4 (SEQ ID NO: 27).

Variant 4: This design combines the principles of Variants 2 and 3 together to account for a potential secondary issue. Prior literature has demonstrated that slpA owes its expression strength to the high degree of mRNA stability afforded by the 5' untranslated region of the promoter (from the TSS to the RBS), which forms a high-free-energy RNA hairpin to protect mRNA species from 5' mediated degradation. See Narita et al. Appl Microbiol Biotechnol 73:366-373 (2006). However, the hairpin is such that the RBS is in a low energy binding region of the hairpin and is thus still accessible to the ribosome. Variants 2 and 3 alter the binding free energy of the mRNA. So, to account for this property, in variant 4 there are 4 tetO boxes in this design: two that are proximal to the Transcriptional start site just as in Variant 2, and two that are proximal to the RBS as in Variant 4. However, the two near the RBS are encoded in reverse complement, evenly spaced from the first two tetO sequences next to the TSS, thus not only preserving, but increasing the mRNA hairpin folding energy (while still leaving the RBS accessible). See FIG. 10.

FIG. 11 depicts minimum free energy mRNA structural folding predictions. Each of these variants was then tested in a plasmid with no TetR (meaning the inserted promoters are not repressed, and should be constitutively active), driving a fluorescent reporter. *E. coli* harboring these plasmids were grown to stationary phase (where wild-type slpA promoter expression is strongest), and all variants exhibited equivalent expression strength to the original promoter. Subsequently, this test was replicated in *L. rhamnosus* GG. In this setting, only variant 2 exhibited measurable expression (3 fold-less than the wild-type promoter). Therefore, only variant 2 was selected for testing in the presence of TetR. The other variants may exhibit function in other strains of *Lactobacilli*, and would as such be rescreened when switching strains. In this vein, the promoter sequence may be further edited to replace the A in the −13 position upstream of the −10 box with a G. 25% of *Lactobacilli* exhibit a TG dinucleotide motif in the −13/−14 positions of their promoter sequences, so when implementing the slpA promoter, or engineered variants thereof, in these strains, this nucleotide substitution may yield more robust expression. See McCracken et al. J Bacteriol 181(20):6569-6572 (1999).

Figure 12:
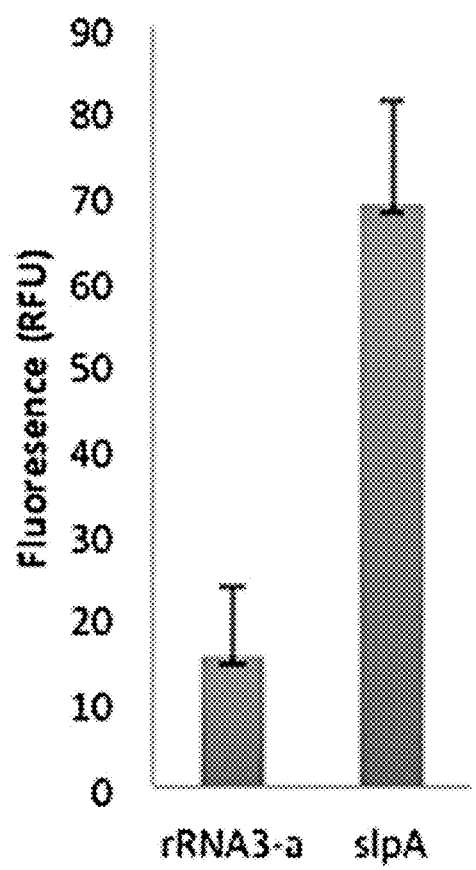
FIG. 12 depicts fluorescence data of relative expression strengths for the promoter for the ribosomal RNA 3-a from *L. plantarum* and slpA.
Figure 13:
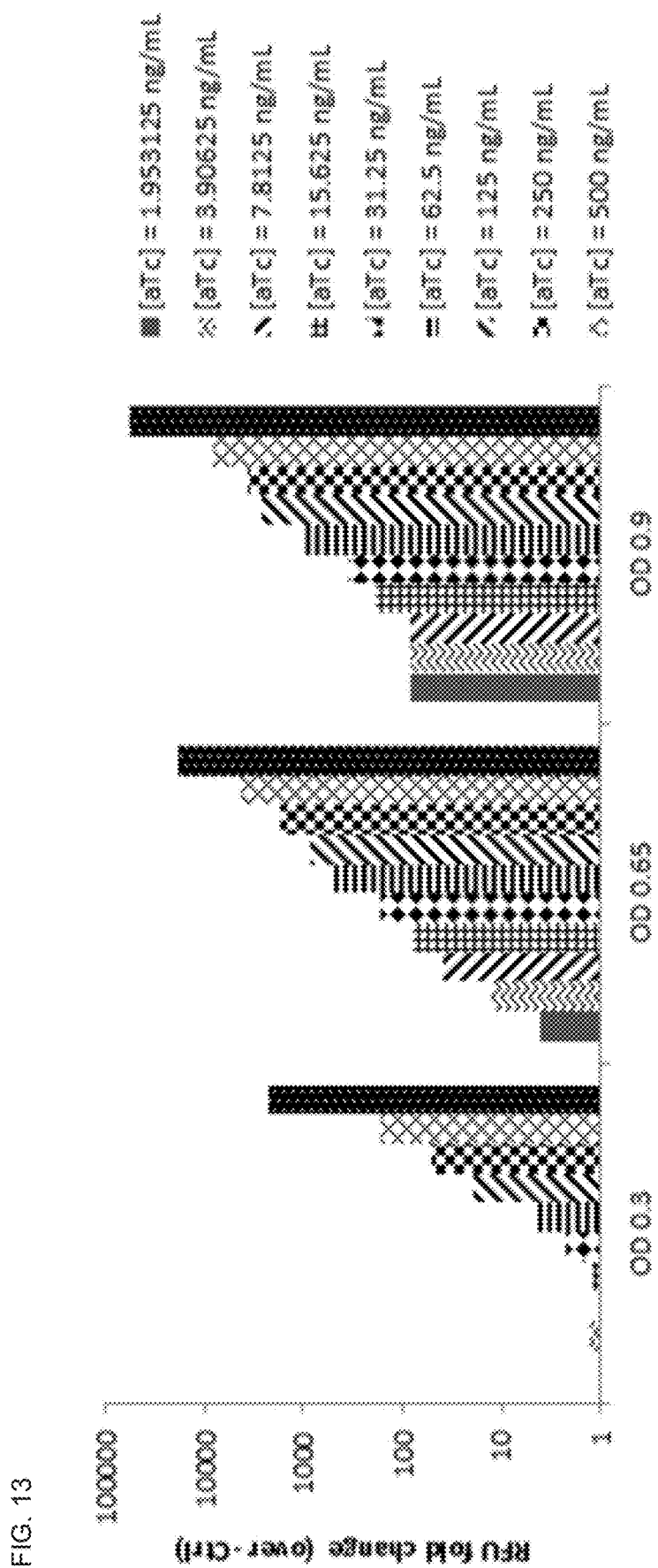
FIG. 13 depicts data demonstrating that slpA with a deletion successfully drives repressor function across a dynamic range of $10^6$ in *E. coli*, when paired with slpA-tetO variant 2.

The TetR coding region from PltetO was then transferred to a plasmid, fused upstream of, but in reverse complement to the promoter, so as to eliminate the potential for transcriptional read through by DNA polymerase between the two. However, no repression of the promoter was observed in *Lactobacillus*, due to the same reason the original PltetO promoter exhibited no function—the promoter driving expression of TetR was not sufficiently active. As such, the promoter sequence was replaced with constitutive promoters native to *Lactobacilli*. Selection of the promoter is important to the repressor function. Weak promoters driving low expression of TetR will result in a "leaky", basal expression in the absence of induction agent. However, TetR has high affinity to the tetO sequence, so overexpression of TetR will reduce the dynamic range of induced expression. Accordingly, the promoter for the ribosomal RNA 3-a from *L. plantarum* was selected, because its expression strength is 5-fold weaker than that of slpA. See FIG. 12. An effective choice for the promoter of TetR is not limited to that of rRNA3-a. Published data indicate that the clpC promoter *L. fermentum* BR11, the lacA promoter from *L. lactis*, the ldh promoter from *L. plantarum*, *L. casei*, or *L. reuteri*, the pgm promoter from *L. agilis*, and the ermB promoter from *E. faecalis*, all are similarly weaker than slpA, and can thus be substituted (see McCracken et al. *Arch Microbiol.* 2000 173:383-389, Miyoshi et al., *FEMS Microbiol. Lett.* 239(2): 205-212 (2004), Lizier et al., *FEMS Microbiol. Lett.* 308: 8-15 (2010) each of which are hereby incorporated by reference in its entirety). By extension, cognate promoters from sister species of the aforementioned organisms may similarly be used. The wild-type slpA promoter itself can also be utilized as the promoter for TetR—with the potential benefit of maximally reducing any leakage from the induction system (basal expression in the absence of an inducer), since it is as strong or stronger than any of the engineered slpA variants. However this may require tuning in order to preserve an optimal dynamic range during induction. Slight weakening of the promoter sequence associated with TetR (referred to as TetR-slpA) via RBS site mutation, deletion or mutation of the upstream promoter element (AAATATTA-CAAATAGTATTTTTCGGTCA (SEQ ID NO: 20), or any subsequence thereof), or mutations introduced into the −35 box, the −10 box, or the sequence space between them, may achieve the desired strength relative to the engineered slpA promoter intended for the target protein (referred to as slpA-target). TetR expression by slpA may also be tuned by the introduction of catabolic repressive elements such as those sensitive to glucose, to thus scale TetR expression by slpA with cellular growth rate. Alternatively, variant 2's design may be applied to TetR-slpA using mutated tetO sequences that bind with lower affinity than the original tetO (e.g. via the introduction of point mutations that break the tetO's sequence palindromes), thus scaling tetR expression with the induction by aTc itself (two candidates with weakly binding tetO mutants include TCTCTAACACTGTTAGGG (SEQ ID NO: 21) and TCTGTATCACTGATACGG (SEQ ID NO: 22), as per Bolinteneau et al. *ACS JCED* 59:3167-3176 (2014) hereby incorporated by reference in its entirety). All designs take into consideration the cloning of apposed slpA promoters that is inherent to the slpA promoter sequence. In *L. acidophilus*, the slpA promoter sequence is naturally apposed, in the same orientation as proposed for TetR-slpA, to promoter sequence for slpB. In nature, the slpA and slpB promoters invert with one another in order to control the expression of their respective proteins. The same occurs if TetR-slpA is in apposition to slpA-target. However, deletion of an invertase recognition site associated with the Din family of invertases (ATCTTGCTTT-GAAGGGTTTTGTACAT (SEQ ID NO: 23) as per Boot et al. *Mol. Microbiol.* 21(4):799-809 (1996) hereby incorporated by reference in its entirety) located between the transcriptional start site and the RBS, together with the introduction of a randomized DNA spacer sequence between the two promoter units (comprised of 30% A, 50% G, and 20% T), resolves this issue (see SEQ ID NO: 3). It is sufficient to delete only one of either invertase sites within TetR-slpA, or slpA-target, though it is preferable to delete the site within TetR-slpA as this lesion disrupts the 5' untranslated region mRNA folding structure described ear-lier. slpA with this deletion successfully drives repressor function across a dynamic range of $10^6$ in *E. coli*, when paired with slpA-tetO variant 2. See FIG. 13.

Embodiments of the present disclosure are directed to an engineered slpA promoter for repression by tetO having the following characteristics. First, for each variant, the tetO boxes can be shifted up to 22 base pairs (i.e. two Kuhn lengths) upstream or downstream from their present locations in the variants. That is, the tetO boxes can be placed within plus or minus 22 base pairs from the location identified in each variant. Second, the function of variant 2 can be readily replicated with any other promoter—since the tetO boxes are located past slpA's transcriptional start site (and regulate promoter function at the stage just after RNA polymerase binding by preventing it from proceeding into the protein reading frame), the sequence region of variant 2 from the transcriptional start site to the RBS can be fused at its 5' end to any promoter within the region of its respective transcriptional start site (see SEQ ID NO: 4, 7). Accordingly, one aspect of the present disclosure is the insertion of one or more tetO boxes within a target promoter's transcriptional start site. Such fusions are shown to either preserve or boost the expression strength of several promoters unrelated to slpA, indicating that the embodiments of the present disclosure are not limited to the promoter slpA and can be replicated for other promoters (see Miyoshi et al., *FEMS Microbiol. Lett.* 239(2):205-212 (2004) hereby incorporated by reference in its entirety). Third, the effect of fusing slpA's 5' untranslated region to any given promoter can similarly be applied to the expression of TetR, if it is desirable to increase its expression strength, or tune its dynamic range via the introduction of tetO sequences (or mutants thereof) as described above for TetR-slpA (exemplified with the *L. fermentum* BR11 ClpC promoter in SEQ ID 7). Fusing the slpA 5' untranslated region which includes one or more operator boxes to any given promoter sequence allows for methods of target nucleic acid expression or repressor expression. Fourth, the expression of TetR may be further modulated by codon engineering. Bacteria have varying tRNA abundances that lead to biased translational efficiencies within sets of degenerate codons. Thus, like codons may be substituted to tune the translational efficiency of TetR. For example, the TetR sequence may be recoded with the most frequently used tRNAs in *Lactobacilli* to optimize translational efficiency in this species (see SEQ ID NO: 5). Lastly, the principles of potential tetO (or any other repressor operator box sequence) variant design can be applied to any other promoter sequence and will be apparent to those of skill in the art based on the present disclosure.

In this expression system, gene expression was orthogonally induced with improved control. This was accomplished by engineering a high-copy plasmid that carries the tetracycline repressor (tetR) paired with the oft used PltetO system, and editing the promoter for s-layer protein A (slpA), which is one of the strongest constitutive promoters known in *Lactobacilli* and has been used to direct heterologous gene expression in a wide range of species (see A. McCracken et at. Analysis of promoter sequences from *Lactobacillus* and *Lactococcus* and their activity in several *Lactobacillus* species. *Arch Microbiol.* 2000 173:383-389 hereby incorporated by reference in its entirety). The slpA promoter was edited by inserting tetracycline repressor protein binding sites (tetO) at a variety of locations that were then screened for function. Several guidelines were designed for promoter design in regards to the placement of tetO. Variant design was dictated by the locations of endogenous repressor binding site locations in *Lactobacilli*, and their endogenous catabolic repressor motifs. Custom bioinformatics were also utilized to generate consensus sequences for *Lactobacillus* promoters in order to identify functionally important sequence spaces to mitigate disruption of promoter function. Lastly, promoter designs were further guided by secondary structure predictions of predicted mRNA.

EXAMPLE II

Orthogonally Induced Gene Expression in *Lactobacilli*

To evaluate the functionality of the aTc induction system described herein in lactic acid bacteria, the TetR regulon described herein is driven by a *L. plantarum* promoter paired with slpA-tetO variant 2 (current SEQ IDs 1 and 2), into *L. rhamnosus* GG via electroporation with a high copy plasmid. Sequence verified colonies, as well as colonies harboring a negative control plasmid with no fluorescence reporter, were then picked in triplicate, and used to inoculate liquid cultures that were grown overnight. These overnight cultures were then sub-cultured 1/100 into fresh media, in duplicate—one culture containing 10 ng/mL aTc, the other containing no inducing agent. The culture with inducing agent, was then serially diluted by 50%, 5 times (yielding cultures with 5, 2.5, 1.25, 0.625, and 0.3125 ng/mL of aTc, in addition to the original 10 ng/mL culture). These cultures were then grown to an optical density of 0.2 (to capture lag phase behavior), 0.6 (log phase), and 1.0 (stationary phase), as measured by an optical cell density meter. At each optical density, the fluorescence of all cultures and replicates were measured in absolute units in a fluorimeter. Relative fluorescence units were then computed as a fold change value over the measured fluorescence of the negative control cell cultures that were known to not express fluorescence protein.

The slpA variant featuring two tetO sites between the transcriptional start site and the ribosome binding site demonstrated reliable repression and expression of a fluorescent protein in the absence and presence of aTc, in *L. rhamnosus* GG—a prevalent probiotic (see FIG. 1). Importantly, control of gene expression in all growth phases: early exponential, mid-exponential, and stationary phase were demonstrated.

Figure 14:
FIG. 14 depicts the results of repression and expression of a fluorescent protein in the absence and presence of aTc in *L. gasseri*.

The functionality of tetracycline induction was similarly demonstrated in the vaginal probiotic strain, *L. gasseri*, indicating the ease of transfer for this system into different strains. In this instance, the TetR regulon of the induction system was expressed by the *E. faecalis* ermB promoter and, as above, paired with the slpA-tetO variant 2 (current SEQ IDs 2 and 6). The experimental procedure used was exactly as described above for *L. rhamnosus* GG, with the exception that the dilution series began at 500 ng/mL aTc (see FIG. 14). Strong expression was driven by tetracycline with this induction system in *L. gasseri*, indicating the versatility of our methodology.

Figure 15:
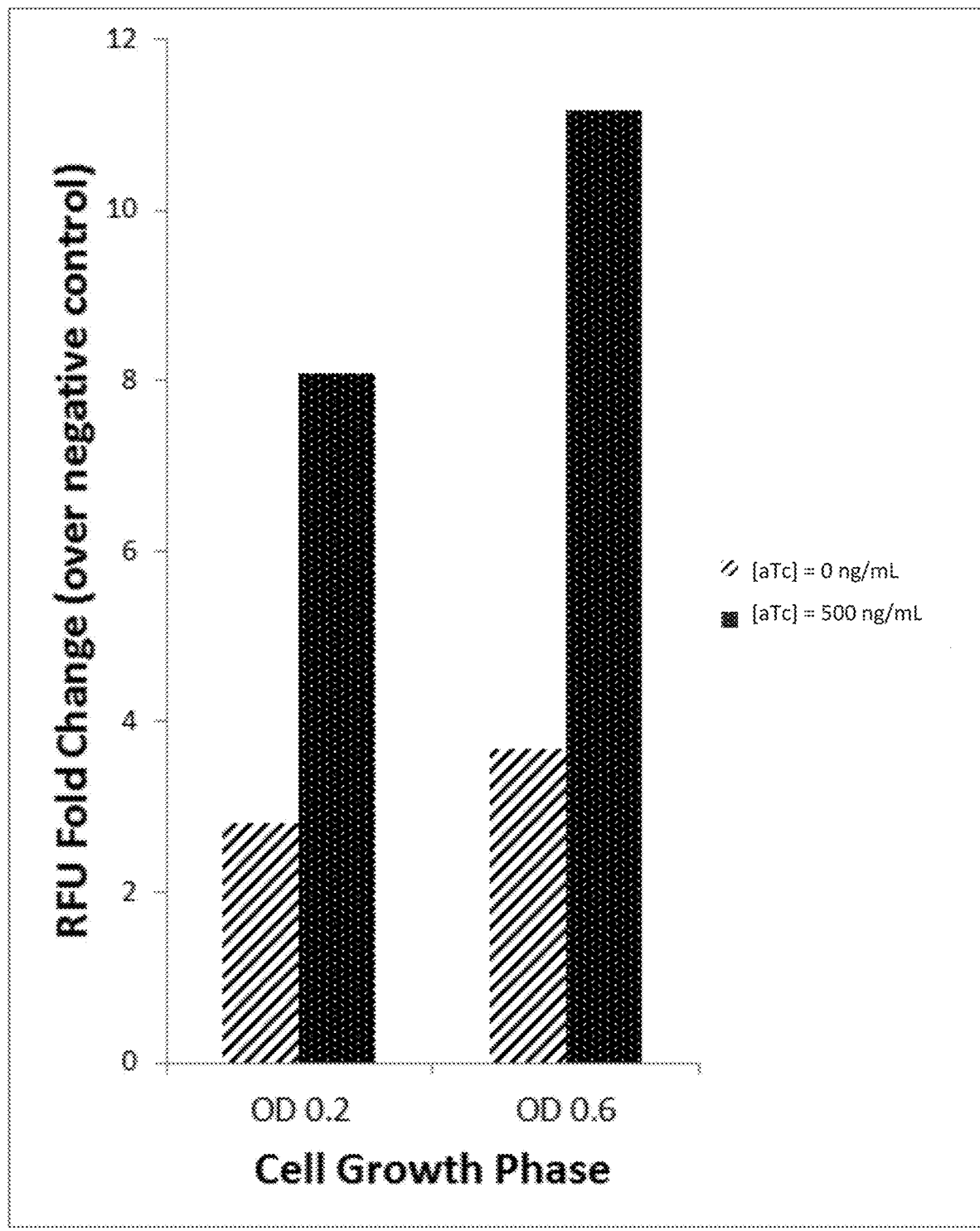
FIG. 15 depicts the results of repression and expression of a fluorescent protein in the absence and presence of aTc in *L. gasseri*, with a hybrid promoter variant.

Under similar experimental conditions, a hybrid promoter in junction with TetR (TetR-ClpC-slpA) in *L. gasseri* was functional, validating the potential use of the strategy for modulating promoter function with the slpA untranslated region, as expounded in previous sections (see FIG. 15).

The functionality of the tetracycline inducible promoters as an orthogonal gene expression system can be further modified and verified in a wider array of strains and cells, and the dynamic range of the promoter can be improved by modulation of basal repression strength. According to certain aspects, methods and expression systems as herein described are provided to control production of proteins by probiotic species such as *L. rhamnosus* GG or *L. gasseri* while in vivo, which aTc has previously enabled in the gut pathogen, *H. pylori*, in mouse models (see A. Debowski et al. Development of a tetracycline-inducible gene expression system for the study of *Helicobacter pylori* pathogenesis. *Appl Environ. Microbiol.* 2013 December; 79(23):7351-59 hereby incorporated by reference in its entirety.

EXAMPLE III aTc-Inducible Promoter Variant

According to one aspect, an aTc-inducible promoter variant is provided. According to an additional aspect, the aTc-inducible promoter variant exhibits low or undetectable levels of leakage. Lowering or preventing leakage is desirable such as in the case of controlling expression of gene editing proteins such as Cas9, where the repressed state ideally has no measurable gene editing activity. In some aspects, replacement of a regulon promoter to address leakage may not be desirable insofar as such a replacement may present incompatibility issues with the host.

According to one aspect, the present disclosure provides methods for creating lower leakage variants of an aTc-inducible promoter. According to one aspect, a promoter variant is provided wherein the sequence space around the tetO binding sites is altered. According to one aspect, a promoter variant is provided wherein the sequence space around the tetO binding sites is altered to more closely mimic the general tetO binding site sequence space as found in PltetO (which exhibits low leakage in *E. coli*).

According to one aspect, an altered promoter sequence is provided where the tetR binding site (or binding landing pad) includes a base pair from PltetO that is one nucleotide upstream to the first tetO binding site (SEQ ID NO:8), the second tetO binding site (SEQ ID NO:9), or both tetO binding sites (SEQ ID NO:10). In this manner, the promoter sequence of SEQ ID NO:2 is altered to extend the tetR binding landing pad by including one additional base pair from PltetO that is one nucleotide upstream to the first, second, or both tetO binding sites as represented in SEQ ID NO:8, SEQ ID NO:9 and SEQ ID NO:10. Crystallographic analysis of the TetR-tetO complex has shown that this particular nucleotide is not a critical participant in TetR binding (see J. L. Ramos et al.). For this reason, carry over of this nucleotide between PltetO and $P_{slpA}$ was omitted in the case of SEQ ID NO:2, in order to better preserve the mRNA secondary structure of the 5'UTR sequence due to its influence on promoter function as described previously. However, it has been shown that substitution at this position from A/T base-pairing to G/C base-pairing (as is the case in SEQ ID NO:2) renders a marginal, but measurable reduction in TetR binding affinity (A. Wissmann et al., Saturation mutagenesis of the Tn10-encoded tet operator $O_1$: Identification of base-pairs involved in Tet repressor recognition. *J. Mol. Bio.* (1988) 202:397-406). According to the present disclosure, retaining an A/T base-pair results in the first tetO binding site sequence with a higher affinity to TetR, and thus a more tightly repressed system. In one embodiment, a promoter sequence has at least 85% homology, at least 90% homology, at least 95% homology, at least 97% homology, at least 98% homology or at least 99% homology to SEQ ID NO:8. In one embodiment, a promoter sequence has at least 85% homology, at least 90% homology, at least 95% homology, at least 97% homology, at least 98% homology or at least 99% homology to SEQ ID NO:9. In one embodiment, a promoter sequence has at least 85% homology, at least 90% homology, at least 95% homology, at least 97% homology, at least 98% homology or at least 99% homology to SEQ ID NO:10.

According to one aspect, an altered promoter sequence is provided where the tetR binding site (or binding landing pad) includes a base pair from PltetO that is one nucleotide downstream to the first tetO binding site (SEQ ID NO:11), the second tetO binding site (SEQ ID NO:12), or both tetO binding sites (SEQ ID NO:13), on its 3' end. In this manner, the promoter sequence of SEQ ID NO:2 is altered to extend the tetR binding landing pad by including one additional base pair from PltetO that is one nucleotide downstream to the first, second, or both tetO binding sites as represented in SEQ ID NO:11, SEQ ID NO:12 and SEQ ID NO:13.

According to one aspect, the inclusion of the original nucleotide that is 1 base-pair downstream of the tetO binding site in PltetO, on its 3' end has the same effect on TetR binding (as including the 1 base-pair upstream of the tetO binding site), as the tetO sequence is palindromic, and each of the opposite ends of the sequence exhibit the same mechanism of interaction with TetR, albeit with distinct (but identical) helix-turn-helix motifs within the TetR dimer. Carrying over this nucleotide to the first, second, or both tetO binding site sequence, and substituting the affinity-reducing G/C base-pair in that region of $P_{slpA}$ results in the more repressive promoter design described by SEQ ID NO:11, 12, and 13. In one embodiment, a promoter sequence has at least 85% homology, at least 90% homology, at least 95% homology, at least 97% homology, at least 98% homology or at least 99% homology to SEQ ID NO:11. In one embodiment, a promoter sequence has at least 85% homology, at least 90% homology, at least 95% homology, at least 97% homology, at least 98% homology or at least 99% homology to SEQ ID NO:12. In one embodiment, a promoter sequence has at least 85% homology, at least 90% homology, at least 95% homology, at least 97% homology, at least 98% homology or at least 99% homology to SEQ ID NO:13.

According to one aspect, an altered promoter sequence is provided that includes the 6 bp sequence found in the PltetO promoter from which the tetO binding site sequences were derived. In this manner, the promoter sequence of SEQ ID NO:2 is altered to include the 6 bp sequence found in the PltetO promoter from which the tetO binding site sequences were derived. The intervening 7 bp sequence—currently 7 bp of the original slpA 5' UTR sequence at that location—is replaced with the 6 bp sequence found in the PltetO promoter from which the tetO binding site sequences were derived (which happens in this case to be the −35 binding site sequence of PltetO). This alteration more closely replicates the DNA helicity and melting temperature of PltetO at this location, as these factors influence the binding energy of the TetR-tetO complex. Reduction of this spacer sequence from 7 to 6 bp also serves to more closely replicate the relative rotational displacement between the tetO contact sites, which may have additional influence on TetR binding kinetics. This results in another, more repressive promoter design variant, represented by SEQ ID NO:14. In one embodiment, a promoter sequence has at least 85% homology, at least 90% homology, at least 95% homology, at least 97% homology, at least 98% homology or at least 99% homology to SEQ ID NO:14.

According to one aspect, a promoter sequence is provided that includes one or more or all of the following: (1) a base pair from PltetO that is one nucleotide upstream to the first tetO binding site, the second tetO binding site, or both tetO binding sites; (2) a base pair from PltetO that is one nucleotide downstream to the first tetO binding site, the second tetO binding site, or both tetO binding sites, on its 3' end; and/or (3) the 6 bp sequence found in the PltetO promoter from which the tetO binding site sequences were derived. According to one aspect, a promoter sequence is provided that includes all of the following: (1) a base pair from PltetO that is one nucleotide upstream to the first tetO binding site, the second tetO binding site, or both tetO binding sites; (2) a base pair from PltetO that is one nucleotide downstream to the first tetO binding site, the second tetO binding site, or both tetO binding sites, on its 3' end; and (3) the 6 bp sequence found in the PltetO promoter from which the tetO binding site sequences were derived.

Relative to SEQ ID NO:2, an aspect of the present disclosure provides one or more base or base pair alterations (i.e., additions or deletions) include the following: (1) one additional base pair upstream of the first tetO binding site, (2) one additional base pair downstream of the second tetO binding site, and/or (3) replacement of the intervening, 7 bp sequence—currently 7 bp of the original slpA 5'UTR sequence at that location—with the 6 bp sequence found in the PltetO promoter from which the tetO binding site sequences were derived (which in an exemplary embodiment is the −35 binding site sequence of PltetO). According to one aspect, the alterations are selected to more closely mimic the general tetO binding site sequence space as found in PltetO (which exhibits low leakage in *E. coli*). In particular, replacement of the intervening, 7 bp sequence between the tetO binding sites to its original identity serves to more closely replicate the DNA helicity and melting temperature of PltetO at this location, as these factors influence the binding energy of the TetR-tetO complex.

Figure 16:
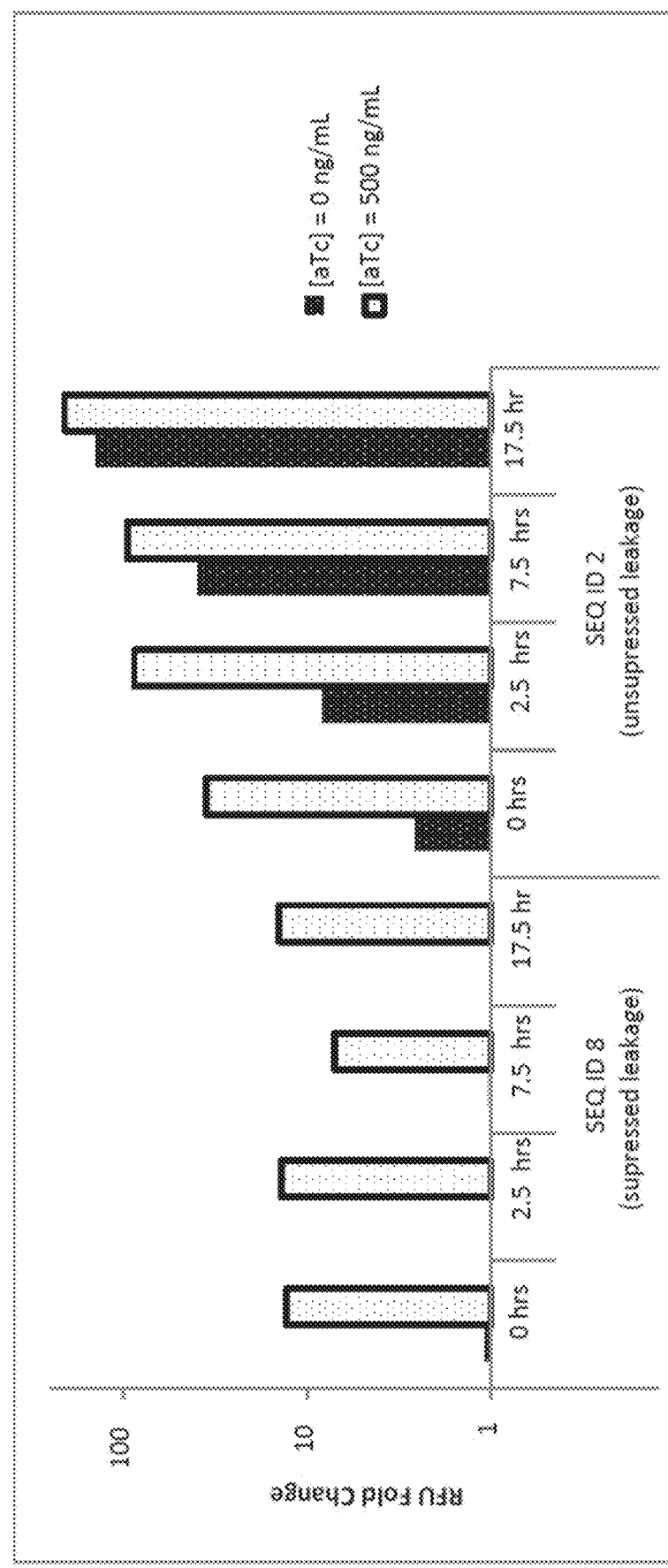
FIG. 16 depicts data showing suppressed leakage of an aTc-inducible slpA promoter variant modified to more closely resemble the general tetO binding site sequence space of PltetO.

An exemplary aTc-inducible slpA promoter variant is provided in SEQ ID NO:15 which includes the alterations above resulting in a combined, maximally repressive variant. In one embodiment, a promoter sequence has at least 85% homology, at least 90% homology, at least 95% homology, at least 97% homology, at least 98% homology or at least 99% homology to SEQ ID NO:15. All of the described alterations work in concert to achieve an inducible system that has essentially undetectable levels of leakage in all phases of growth. Using this aTc-inducible slpA promoter variant of SEQ ID NO:15, no basal expression was detected in the absence of aTc, whether at stationary phase for 0 hours, 2.5 hours, 7.5 hours, and 17.5 hours, as exemplified in *L. rhamnosus* GG (see FIG. 16). FIG. 16 also shows an order of magnitude (10×) reduction in maximum inducible expression.

EXAMPLE 4

Induction of Antibody Fragment Protein Secretion in *Lactobacillus* Via aTc

The engineered aTc-inducible slpA promoter has been valuable for enabling heterologous protein secretion in *Lactobacillus*. When secreting heterologous proteins via the Type I secretion system in *Lactobacilli* (or any bacterial or fungal strain), toxicity can be an issue that prevents successful secretion, especially when driving expression of a secreted protein with a strong promoter—this is because it may overload host cell secretion machinery at the expense of proteins that are naturally secreted by the same pathway that are necessary for survival. As a result, genetic engineering of expression cassettes for secreted proteins is problematic due to frame-shift mutations that prevent protein expression or secretion. This is because cells that secrete toxic levels of heterologous proteins are outcompeted by cells that generate mutations that prevent it in culture, making it difficult to isolate cells that harbor intact genetic elements encoding the desired secretory activity.

Figure 17:
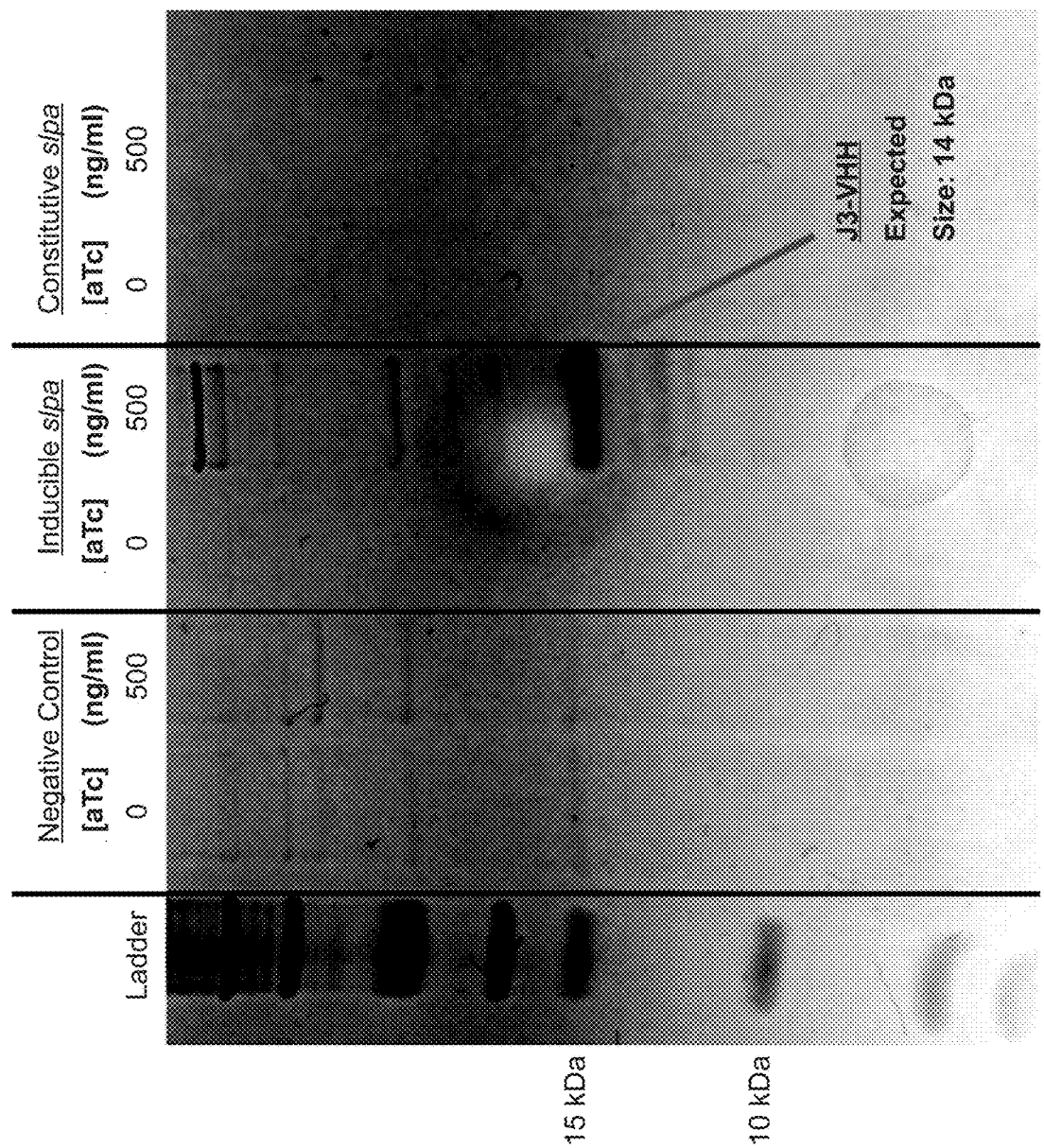
FIG. 17 is a gel image of an experiment showing expression of HisTagged, anti-HIV (gp120) camelid nanobody (J3-VHH) using an aTc-inducible expression cassette encoding J3-VHH secretion.

According to one aspect, an inducible expression system is used prevent expression during bacterial culture and clone isolation. According to one aspect, expression is controlled and kept off during bacterial culture and clone isolation to avoid or lower or reduce or inhibit secretion-induced toxicity. According to one aspect, the level of a HisTagged, anti-HIV (gp120) camelid nanobody (J3-VHH) purified from culture supernatant, when secretion of protein was driven by an inducible system (SEQ ID NO: 2) was compared to a system using an uncontrolled, constitutive slpA. Cells (in this case, *L. gasseri*) without an expression cassette (negative control with no protein expected), an aTc-inducible expression cassette encoding J3-VHH secretion, and an equivalent, but constitutive expression cassette, were grown in culture to an optical density of 0.4 (the start of the exponential growth phase, during which time cellular protein production capacity is maximal), and split into two equal volumes—500 ng/mL of aTc was added to one, while the other received no aTc (as an internal negative control to verify functional induction). Only cells with the inducible cassette that received aTc secreted any protein into the supernatant—as shown by protein gel electrophoresis of HisTag purified *L. gasseri* culture supernatant of FIG. 17. Subsequent sequencing analysis showed that the majority of *L. gasseri* cells that carried the constitutive expression cassette acquired mutations that stopped expression and secretion of J3-VHH, while cells with the inducible cassette remained genetically intact.

Sequences

TetR-3a regulon: (SEQ ID NO: 1)
5'-
**TTATAAAAAGATGTTGACAGCTTGTTCTGATGATGATAAACTTTAATAGTTG
CGAGAGAAAGAGGAGAAATACTAG**[1]ATGATGTCTAGATTAGATAAAAGTAAAG
TGATTAACAGCGCATTAGAGCTGCTTAATGAGGTCGGAATCGAAGGTTTAACAA
CCCGTAAACTCGCCCAGAAGCTAGGTGTAGAGCAGCCTACATTGTATTGGCATGT
AAAAAATAAGCGGGCTTTGCTCGACGCCTTAGCCATTGAGATGTTAGATAGGCA
CCATACTCACTTTTGCCCTTTAGAAGGGGAAAGCTGGCAAGATTTTTTACGTAAT
AACGCTAAAAGTTTTAGATGTGCTTTACTAAGTCATCGCGATGGAGCAAAAGTAC
ATTTAGGTACACGGCCTACAGAAAAACAGTATGAAACTCTCGAAAATCAATTAG
CCTTTTTATGCCAACAAGGTTTTTCACTAGAGAATGCATTATATGCACTCAGCGC
TGTGGGGCATTTTACTTTAGGTTGCGTATTGGAAGATCAAGAGCATCAAGTCGCT
AAAGAAGAAAGGGAAACACCTACTACTGATAGTATGCCGCCATTATTACGACAA
GCTATCGAATTATTTGATCACCAAGGTGCAGAGCCAGCCTTCTTATTCGGCCTTG
AATTGATCATATGCGGATTAGAAAAACAACTTAAATGTGAAAGTGGGTCTTAA[2]-3'
1. *L. plantarum* ribosomal RNA promoter 3-a
2. TetR coding region TetR coding region, codon optimized for *Lactobacillus* (SEQ ID NO: 5):
5'-
ATGATGTCACGCTTGGATAAATCAAAAGTTATTAATTCAGCATTGGAATTGTTGA
ATGAAGTTGGCATTGAAGGCTTGACCACCCGCAAATTGGCACAAAAATTGGGCG
TTGAACAACCAACCTTGTATTGGCATGTTAAAAATAAACGCGCATTGTTGGATGC
ATTGGCAATTGAAATGTTGGATCGCCATCATACCCATTTTTGCCCATTGGAAGGC
GAATCATGGCAAGATTTTTTGCGCAATAATGCAAAATCATTTCGCTGCGCATTGT
TGTCACATCGCGATGGCGCAAAAGTTCATTTGGGCACCCGCCCAACCGAAAAAC
AATATGAAACCTTGGAAAATCAATTGGCATTTTTGTGCCAACAAGGCTTTTCATT
GGAAAATGCATTGTATGCATTGTCAGCAGTTGGCCATTTTACCTTGGGCTGCGTT
TTGGAAGATCAAGAACATCAAGTTGCAAAAGAAGAACGCGAAACCCCAACCACC
GATTCAATGCCACCCATTGTTGCGCCAAGCAATTGAATTGTTTGATCATCAAGGCG
CAGAACCAGCATTTTTGTTTGGCTTGGAATTGATTATTTGCGGCTTGGAAAAACA
ATTGAAATGCGAATCAGGCTCATAA-3'

TetR-slpA regulon with Din invertase site removed (SEQ ID NO: 3):
5'-
*CCCCTTCTACCATACCCCCTTTACACCTACTCCACCTCTATATTCCATCC*[1]TGCTTG
TGGGGGTAAGCGGTAGGTGAAATATTACAAATAGTATTTTTCGGTCATTTTA
ACTTGCTATTTCTTGAAGAGGTTAGTACAATATGAATC*G*[2]TGGTAAGTAATAG
GACGTGCTTCAGGCGTGTTGCCTGTACGCATGCTGATTCTTCAGCAAGACTA
CTACCTCATGAGAGTTATAGACTCATGGTATAGGCTCCTATCACATGCTGAA
CCTATGGCCTATTACATTTTTTTATATTTC*AAGGAGG*[3]AAAAGACCACATGATG
TCTAGATTAGATAAAAGTAAAGTGATTAACAGCGCATTAGAGCTGCTTTAATGAGGTCGG
AATCGAAGGTTTAACAACCCGTAAACTCGCCCAGAAGCTAGGTGTAGAGCAGCCTACAT
TGTATTGGCATGTAAAAAATAAGCGGGCTTTGCTCGACGCCTTAGCCATTGAGATGTTAG
ATAGGCACCATACTCACTTTTGCCCTTTAGAAGGGGAAAGCTGGCAAGATTTTTTACGTA
ATAACGCTAAAAGTTTTAGATGTGCTTTACTAAGTCATCGCGATGGAGCAAAAGTACATT
TAGGTACACGGCCTACAGAAAAACAGTATGAAACTCTCGAAAATCAATTAGCCTTTTTAT
GCCAACAAGGTTTTTCACTAGAGAATGCATTATATGCACTCAGCGCTGTGGGGCATTTTA
CTTTAGGTTGCGTATTGGAAGATCAAGAGCATCAAGTCGCTAAAGAAGAAAGGGAAACA
CCTACTACTGATAGTATGCGGCCATTATTACGACAAGCTATCGAATTATTTGATCACCAA
GGTGCAGAGCCAGCCTTCTTATTCGGCCTTGAATTGATCATATGCGGATTAGAAAAACAA
CTTAAATGTGAAAGTGGGTCTTAA[4]-3'
1. Spacer sequence
2. Transcriptional Start Site
3. Ribosomal Binding Site
4. TetR codon region

Sequences

Edited slpA promoter sequence: (SEQ ID NO: 2)
5'-
TGCTTGTGGGGGTAAGCGGTAGGTGAAATATTACAAATAGTATTTTTCGGTCATT
TTAACTTGCTATTTCTTGAAGAGGTTAGTACAATATGAATCG[1]TGG**CCCTATCAG
TGATAGAGA[2]TCAGGCGCCCTATCAGTGATAGAGA**[3]TGATTCTTCAGCAAGACT
ACTACCTCATGAGAGTTATAGACTCATGGATCTTGCTTTGAAGGGTTTTGTACATT
ATAGGCTCCTATCACATGCTGAACCTATGGCCTATTACATTTTTTATATTTCA**AG
GAGG**[4]AAAAGACCAC-3'
1. Transcriptional start site
2. TetR binding site
3. TetR binding site
4. Ribosomal binding site slpA 5' untranslated region for hybrid promoter fusions: (SEQ ID NO: 4)
5'-
G[1]TGGTAAGTAATAGGACGTGCT[2]TCAGGCGTGTTGCCTGTACGCATGC[3]TGAT
TCTTCAGCAAGACTACTACCTCATGAGAGTTATAGACTCATGGATCTTGCTTTGA
AGGGTTTTGTACATTATAGGCTCCTATCACATGCTGAACCTATGGCCTATTACATT
TTTTTATATTTCAAGGAGG[4]AAAAGACCAC-3'-1, Transcriptional start site
2. Sequence space that can be substituted with repressor binding site
3. Sequence space that can be substituted with repressor binding site
4. Ribosomal binding site TetR-ermB regulon: (SEQ ID NO: 6)
5'-
**CTTAAAATATAGTCATAGAATTAGGGCGTCGGTTTTAAAAGTGTGGTAAAAT
AATGGTCAAGATTA**[1]ATGATGTCTAGATTAGATAAAAGTAAAGTGATTAACAGC
GCATTAGAGCTGCTTAATGAGGTCGGAATCGAAGGTTTAACAACCCGTAAACTC
GCCCAGAAGCTAGGTGTAGAGCAGCCTACATTGTATTGGCATGTAAAAAATAAG
CGGGCTTTGCTCGACGCCTTAGCCATTGAGATGTTAGATAGGCACCATACTCACT
TTTGCCCTTTAGAAGGGGAAAGCTGGCAAGATTTTTTACGTAATAACGCTAAAAG
TTTTAGATGTGCTTTACTAAGTCATCGCGATGGAGCAAAAGTACATTTAGGTACTA
CGGCCTACAGAAAAACAGTATGAAACTCTCGAAAATCAATTAGCCTTTTTATGCC
AACAAGGTTTTTCACTAGAGAATGCATTATATGCACTCAGCGCTGTGGGCATTT
TACTTTAGGTTGCGTATTGGAAGATCAAGAGCATCAAGTCGCTAAAGAAGAAAG
GGAAACACCTACTACTGATAGTATGCCGCCATTATTACGACAAGCTATCGAATTA
TTTGATCACCAAGGTGCAGAGCCAGCCTTCTTATTCGGCCTTGAATTGATCATAT
GCGGATTAGAAAAACAACTTAAATGTGAAAGTGGGTCTTAA[2]-3'
1. *E. faecalis* ermB promoter
2. TetR coding region TetR-clpC-slpA hybrid regulon: (SEQ ID NO: 7)
5'-
**CTTAAAATATAGTCATAGAATTAGGGCGTCGGTTTTAAAAGTGTGGTAAAAT
AATGGTCAAGATTA[1]GTGGTAAGTAATAGGACGTGCTTCAGGCGTGTTGCCT
GTACGCATGCTGATTCTTCAGCAAGACTACTACCTCATGAGAGTTATAGACT
CATGGTATAGGCTCCTATCACATGCTGAACCTATGGCCTATTACATTTTTTT
ATATTTCAAGGAGGAAAAGACCAC**[2]ATGATGTCACGCTTGGATAAATCAAAAGT
TATTAATTCAGCATTGGAATTGTTGAATGAAGTTGGCATTGAAGGCTTGACCACC
CGCAAATTGGCACAAAAATTGGGCGTTGAACAACCAACCTTGTATTGGCATGTTA
AAAATAAACGCGCATTGTTGGATGCATTGGCAATTGAAATGTTGGATCGCCATCA
TACCCATTTTTGCCCATTGGAAGGCGAATCATGGCAAGATTTTTTGCGCAATAAT
GCAAAATCATTTCGCTGCGCATTGTTGTCACATCGCGATGGCGCAAAAGTTCATT
TGGGCACCCGCCCAACCGAAAAACAATATGAAACCTTGGAAAATCAATTGGCAT
TTTTGTGCCAACAAGGCTTTTCATTGGAAAATGCATTGTATGCATTGTCAGCAGTT
GGCCATTTTACCTTGGGCTGCGTTTTGGAAGATCAAGAACATCAAGTTGCAAAAG
AAGAACGCGAAACCCCAACCACCGATTCAATGCCACCATTGTTGCGCCAAGCAA
TTGAATTGTTTGATCATCAAGGCGCAGAACCAGCATTTTTGTTTGGCTTGGAATT
GATTATTTGCGGCTTGGAAAAACAATTGAAATGCGAATCAGGCTCATAA[3]-3'
1. *L. fermentem* BR11 ClpC promoter
2. slpA 5' untranslated region fragment (see Seq ID 4)
3. TetR codon region SEQ ID NO: 8 Suppressed leakage slpA promoter 1
5'-
TGCTTGTGGGGGTAAGCGGTAGGTGAAATATTACAAATAGTATTTTTCGGTCATT
TTAACTTGCTATTTCTTGAAGAGGTTAGTACAATATGAATCG[1]TGGT[2]**CCCTATCA
GTGATAGAGA[3]TCAGGCGCCCTATCAGTGATAGAGA**[4]TGATTCTTCAGCAAGAC
TACTACCTCATGAGAGTTATAGACTCATGGATCTTGCTTTGAAGGGTTTTGTACAT
TATAGGCTCCTATCACATGCTGAACCTATGGCCTATTACATTTTTTTATATTTCA**A
GGAGG**[5]AAAAGACCAC-3'
1. Transcriptional start site
2. Original base pair 5' to TetR binding site in PltetO
3. TetR binding site
4. TetR binding site
5. Ribosome binding site

| Sequences |
|---|
| SEQ ID NO: 9 Suppressed leakage slpA promoter 2<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGCCCTATCAG<br>TGATAGAGA$^2$TCAGGCT$^3$CCCTATCAGTGATAGAGA$^4$TGATTCTTCAGCAAGACT<br>ACTACCTCATGAGAGTTATAGACTCATGGATCTTGCTTTGAAGGGTTTTGTACATT<br>ATAGGCTCCTATCACATGCTGAACCTATGGCCTATTACATTTTTTATATTTCAAG<br>GAGG$^5$AAAAGACCAC-3'<br>1. Transcriptional start site<br>2. TetR binding site<br>3. Original base pair 5' to TetR binding site in PltetO<br>4. TetR binding site<br>5. Ribosome binding site<br><br>SEQ ID NO: 10 Suppressed leakage slpA promoter 3<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGT$^2$CCCTATCA<br>GTGATAGAGA$^3$TCAGGCT$^4$CCCTATCAGTGATAGAGA$^5$TGATTCTTCAGCAAGA<br>CTACTACCTCATGAGAGTTATAGACTCATGGATCTTGCTTTGAAGGGTTTTGTAC<br>ATTATAGGCTCCTATCACATGCTGAACCTATGGCCTATTACATTTTTTATATTTC<br>AAGGAGG$^6$AAAAGACCAC-3'<br>1. Transcriptional start site<br>2. Original base pair 5' to TetR binding site in PltetO<br>3. TetR binding site<br>4. Original base pair 5' to TetR binding site in PltetO<br>5. TetR binding site<br>6. Ribosome binding site<br><br>SEQ ID NO: 11 Suppressed leakage slpA promoter 4<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGCCCTATCAG<br>TGATAGAGA$^2$T$^3$AGGCGCCCTATCAGTGATAGAGA$^4$TGATTCTTCAGCAAGACT<br>ACTACCTCATGAGAGTTATAGACTCATGGATCTTGCTTTGAAGGGTTTTGTACATT<br>ATAGGCTCCTATCACATGCTGAACCTATGGCCTATTACATTTTTTATATTTCAAG<br>GAGG$^5$AAAAGACCAC-3'<br>1. Transcriptional start site<br>2. TetR binding site<br>3. Original base pair 3' to TetR binding site in PltetO<br>4. TetR binding site<br>5. Ribosome binding site<br><br>SEQ ID NO: 12 Suppressed leakage slpA promoter 5<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGCCCTATCAG<br>TGATAGAGA$^2$TCAGGCGCCCTATCAGTGATAGAGA$^3$T$^4$ATTCTTCAGCAAGACTA<br>CTACCTCATGAGAGTTATAGACTCATGGATCTTGCTTTGAAGGGTTTTGTACATTA<br>TAGGCTCCTATCACATGCTGAACCTATGGCCTATTACATTTTTTATATTTCAAGG<br>AGG$^5$AAAAGACCAC-3'<br>1. Transcriptional start site<br>2. TetR binding site<br>3. TetR binding site<br>4. Original base pair 3' to TetR binding site in PltetO<br>5. Ribosome binding site<br><br>SEQ ID NO: 13 Supressed leakage slpA promoter 6<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGCCCTATCAG<br>TGATAGAGA$^2$T$^3$AGGCGCCCTATCAGTGATAGAGA$^4$T$^5$ATTCTTCAGCAAGACTA<br>CTACCTCATGAGAGTTATAGACTCATGGATCTTGCTTTGAAGGGTTTTGTACATTA<br>TAGGCTCCTATCACATGCTGAACCTATGGCCTATTACATTTTTTATATTTCAAGG<br>AGG$^6$AAAAGACCAC-3'<br>1. Transcriptional start site<br>2. TetR binding site<br>3. Original base pair 3' to TetR binding site in PltetO<br>4. TetR binding site<br>5. Original base pair 3' to TetR binding site in PltetO<br>6. Ribosome binding site<br><br>SEQ ID NO: 14 Suppressed leakage slpA promoter 7<br>5'-<br>TGCTTGTGGGGGTAAGCGGTAGGTGAAATATTACAAATAGTATTTTCGGTCATT<br>TTAACTTGCTATTTCTTGAAGAGGTTAGTACAATATGAATCG$^1$TGGCCCTATCAG<br>TGATAGAGA$^2$*TTGACA*$^3$CCCTATCAGTGATAGAGA$^4$TGATTCTTCAGCAAGACT |

| Sequences |
|---|
| ACTACCTCATGAGAGTTATAGACTCATGGATCTTGCTTTGAAGGGTTTTGTACATT<br>ATAGGCTCCTATCACATGCTGAACCTATGGCCTATTACATTTTTTTATATTTCAAG<br>GAGG[5]AAAAGACCAC-3'<br>1. Transcriptional start site<br>2. TetR binding site<br>3. Original intervening sequence (-35 binding site) between TetR binding sites in PltetO<br>4. TetR binding site<br>5. Ribosome binding site<br><br>SEQ ID NO: 15 Supressed leakage slpA promoter 8<br>5'-<br>TGCTTGTGGGGGTAAGCGGTAGGTGAAATATTACAAATAGTATTTTTCGGTCATT<br>TTAACTTGCTATTTCTTGAAGAGGTTAGTACAATATGAATCG[1]TGGT[2]CCCTATCA<br>GTGATAGAGA[3]*TTGACA*[4]TCCCTATCAGTGATAGAGA[5]T[6]ATTCTTCAGCAAGAC<br>TACTACCTCATGAGAGTTATAGACTCATGGATCTTGCTTTGAAGGGTTTTGTACAT<br>TATAGGCTCCTATCACATGCTGAACCTATGGCCTATTACATTTTTTTATATTTCAA<br>GGAGG[7]AAAAGACCAC-3'<br>1. Transcriptional start site<br>2. Original base pair 5' to TetR binding site in PltetO<br>3. TetR binding site<br>4. Original intervening sequence (-35 binding site) between TetR binding sites in PltetO<br>5. TetR binding site<br>6. Original base pair 5' to TetR binding site in PltetO<br>7. Ribosome binding site |

The invention claimed is:

1. A genetically engineered lactic acid bacterial cell comprising:
   an agent-responsive element having a promoter and one or more transcription repressor protein binding sites,
   wherein the agent-responsive element is operably linked to a target nucleic acid sequence,
   wherein the agent-responsive element has at least 97% homology to a nucleic acid sequence selected from the group consisting of SEQ ID NOs: 2, 8, 9, 10, 11, 12, 13, 14, and 15,
   wherein a transcription repressor protein is bound to the one or more transcription repressor protein binding sites, and
   wherein transcription of the target nucleic acid sequence into a corresponding mRNA is initiated upon binding of a cognate binding agent to the transcription repressor protein causing an allosteric or conformational change to the transcription repressor protein releasing the transcription repressor protein from the one or more transcription repressor protein binding sites.

2. The genetically engineered lactic acid bacterial cell of claim 1, wherein the one or more transcriptional repressor protein binding sites is TetO, the transcriptional repressor protein is TetR, and the cognate binding agent is tetracycline.

3. The genetically engineered lactic acid bacterial cell of claim 1, wherein the lactic acid bacterial cell is within the order Lactobacillales.

4. The genetically engineered lactic acid bacterial cell of claim 1, wherein the lactic acid bacterial cell is selected from the group consisting of *Lactobacillus, Leuconostoc, Pediococcus, Lactococcus, Streptococcus, Carnobacterium, Enterococcus, Oenococcus, Tetragenococcus, Vagococcus,* and *Weisella*.

5. The genetically engineered lactic acid bacterial cell of claim 1, wherein the lactic acid bacterial cell is selected from the group consisting of *Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus alvei, Lactobacillus alvi, Lactobacillus amylolyticus, Lactobacillus amylophilus, Lactobacillus amylotrophicus, Lactobacillus amylovorus, Lactobacillus animalis, Lactobacillus animata, Lactobacillus antri, Lactobacillus apinorum, Lactobacillus apis, Lactobacillus apodemi, Lactobacillus aquaticus, Lactobacillus aviarius, Lactobacillus backii, Lactobacillus bifermentans, Lactobacillus bombi, Lactobacillus bombicola, Lactobacillus brantae, Lactobacillus brevis, Lactobacillus brevisimilis, Lactobacillus buchneri, Lactobacillus cacaonum, Lactobacillus camelliae, Lactobacillus capillatus, Lactobacillus casei, Lactobacillus paracasei, Lactobacillus zeae, Lactobacillus catenefornis, Lactobacillus ceti, Lactobacillus coleohominis, Lactobacillus colini, Lactobacillus collinoides, Lactobacillus composti, Lactobacillus concavus, Lactobacillus coryniformis, Lactobacillus crispatus, Lactobacillus crustorum, Lactobacillus curieae, Lactobacillus curvatus, Lactobacillus delbrueckii, Lactobacillus dextrinicus, Lactobacillus dioliforans, Lactobacillus equi, Lactobacillus equicursoris, Lactobacillus equigenerosi, Lactobacillus fabifermentans, Lactobacillus faecis, Lactobacillus faeni, Lactobacillus farciminis, Lactobacillus farraginis, Lactobacillus fermentum, Lactobacillus floricola, Lactobacillus forum, Lactobacillus formosensis, Lactobacillus fornicalis, Lactobacillus fructivorans, Lactobacillus frumenti, Lactobacillus fuchuensis, Lactobacillus furfuricola, Lactobacillus futsaii, Lactobacillus gallinarum, Lactobacillus gasseri, Lactobacillus gastricus, Lactobacillus ghanensis, Lactobacillus gigeriorum, Lactobacillus ginsenosidimutans, Lactobacillus gorillae, Lactobacillus graminis, Lactobacillus guizhouensis, Lactobacillus halophilus, Lactobacillus hammesii, Lactobacillus hamsteri, Lactobacillus harbinensis, Lactobacillus hayakitensis, Lactobacillus heilongjiangensis, Lactobacillus helsingborgensis, Lactobacillus helveticus, Lactobacillus herbarum, Lactobacillus heterohiochii, Lactobacillus hilgardii, Lactobacillus hokkaidonensis, Lactobacillus hominis, Lactobacillus homohiochii, Lactobacillus hordei, Lactobacillus iatae, Lactobacillus iners, Lactobacillus ingluviei, Lactobacillus insectis, Lactobacillus insicii, Lactobacillus intermedius, Lactobacillus intestinalis, Lactobacillus iwatensis, Lactobacillus ixorae, Lactobacillus japonicus, Lactobacillus jensenii, Lactobacillus johnsonii, Lactobacillus kalixensis, Lactobacillus kefiranofaciens, Lactobacillus kefiri, Lactobacillus kimbladii, Lactobacillus kimchicus, Lactobacillus kimchiensis, Lactobacillus kisonensis, Lactobacillus kitasatonis, Lactobacillus koreensis, Lactobacillus kullabergensis, Lactobacillus kunkeei, Lactobacillus larvae, Lactobacillus leichmannii, Lactobacillus letivazi, Lactobacillus lindneri, Lactobacillus malefermentans, Lactobacillus mali, Lactobacillus manihotivorans, Lactobacillus mellifer, Lactobacillus mellis, Lactobacillus melliventris, Lactobacillus micheneri, Lactobacillus mindensis, Lactobacillus mixtipabuli, Lactobacillus mobilis, Lactobacillus modestisalitolerans, Lactobacillus mucosae, Lactobacillus mudanjiangensis, Lactobacillus murinus, Lactobacillus nagelii, Lactobacillus namurensis, Lactobacillus nantensis, Lactobacillus nasuensis, Lactobacillus nenjiangensis, Lactobacillus nodensis, Lactobacillus odoratitofui, Lactobacillus oeni, Lactobacillus oligofermentans, Lactobacillus ori, Lactobacillus oryzae, Lactobacillus otakiensis, Lactobacillus ozensis, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pasteurii, Lactobacillus paucivorans, Lactobacillus pentosus, Lactobacillus perolens, Lactobacillus plajomi, Lactobacillus plantarum, Lactobacillus pobuzihii, Lactobacillus pontis, Lactobacillus porcinae, Lactobacillus psittaci, Lactobacillus rapi, Lactobacillus rennanquilfy, Lactobacillus rennini, Lactobacillus reuteri, Lactobacillus rhamnosus, Lactobacillus rodentium, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus saniviri, Lactobacillus satsumensis, Lactobacillus secaliphilus, Lactobacillus selangorensis, Lactobacillus senioris, Lactobacillus senmaizukei, Lactobacillus sharpeae, Lactobacillus shenzhenensis, Lactobacillus sicerae, Lactobacillus silagei, Lactobacillus siliginis, Lactobacillus similis, Lactobacillus songhuajiangensis, Lactobacillus spicheri, Lactobacillus sucicola, Lactobacillus suebicus, Lactobacillus sunkii, Lactobacillus taiwanensis, Lactobacillus thailandensis, Lactobacillus tucceti, Lactobacillus ultunensis, Lactobacillus uvarum, Lactobacillus vaccinostercus, Lactobacillus vaginalis, Lactobacillus vermiforme, Lactobacillus vespulae, Lactobacillus vini, Lactobacillus wasatchensis, Lactobacillus xiangfangensis, Lactobacillus yonginensis,* and *Lactobacillus zymae*.

6. The genetically engineered lactic acid bacterial cell of claim 1, wherein the promoter sequence is the slpA promoter sequence.

7. The genetically engineered lactic acid bacterial cell of claim 1, wherein the one or more transcription repressor proteins is a tetracycline repressor protein (TetR).

8. The genetically engineered lactic acid bacterial cell of claim 1, wherein the one or more transcription repressor protein binding sites is a tetracycline repressor protein binding site.

9. The genetically engineered lactic acid bacterial cell of claim 8, wherein the agent-responsive element has two tetracycline repressor protein binding sites between a transcriptional start site and a ribosome binding site.

10. The genetically engineered lactic acid bacterial cell of claim 1, wherein the agent-responsive element has at least 98%, or at least 99% homology to SEQ ID NO: 2.

11. The genetically engineered lactic acid bacterial cell of claim 1, wherein the target nucleic acid sequence encodes a therapeutic protein, a diagnostic protein, a reporter gene, or an enzyme.

12. The genetically engineered lactic acid bacterial cell of claim 1, wherein the target nucleic acid sequence encodes an antibody.

13. The genetically engineered lactic acid bacterial cell of claim 1, wherein the target nucleic acid sequence encodes a Cas9 protein, a Cas9 nuclease, a Cas9 nickase, a nuclease null Cas9 protein, a spCas9 nuclease, a spCas9 nickase, a nuclease null spCas9 protein, a Cpfl nuclease, a Cpfl nickase, a nuclease null Cpfl protein, a C2c2 nuclease, a C2c2 nickase, or a nuclease null C2c2 protein.

14. The genetically engineered lactic acid bacterial cell of claim 1, wherein the target nucleic acid sequence encodes a fluorescent protein or a luminescent protein.

15. The genetically engineered lactic acid bacterial cell of claim 1, wherein the agent-responsive element, having a promoter and one or more transcription repressor protein binding sites operably linked to a target nucleic acid sequence, is included in an episomal vector or is integrated into cellular chromosomal DNA.

16. The genetically engineered lactic acid bacterial cell of claim 1, wherein the agent-responsive element has a plurality of tetracycline repressor protein binding sites between a transcriptional start site and a ribosome binding site.

17. A method for controlling the expression of a target protein by a genetically engineered lactic acid bacterial cell within a subject comprising
introducing into the subject the genetically engineered lactic acid bacterial cell or a population of genetically engineered lactic acid bacterial cells of claim 1,
and providing the subject with a cognate binding agent which binds to the one or more transcriptional repressor proteins to activate the promoter and induce transcription of the target nucleic acid sequences.

18. The genetically engineered lactic acid bacterial cell of claim 1, wherein the agent-responsive element has at least 98% homology to SEQ ID NO: 8, at least 99% homology to SEQ ID NO: 8, or is SEQ ID NO: 8.

19. The genetically engineered lactic acid bacterial cell of claim 1, wherein the agent-responsive element has at least 98% homology to SEQ ID NO: 9, at least 99% homology to SEQ ID NO: 9, or is SEQ ID NO: 9.

20. The genetically engineered lactic acid bacterial cell of claim 1, wherein the agent-responsive element has at least 98% homology to SEQ ID NO: 10, at least 99% homology to SEQ ID NO: 10, or is SEQ ID NO: 10.

21. The genetically engineered lactic acid bacterial cell of claim 1, wherein the agent-responsive element has at least 98% homology to SEQ ID NO: 11, at least 99% homology to SEQ ID NO: 11, or is SEQ ID NO: 11.

22. The genetically engineered lactic acid bacterial cell of claim 1, wherein the agent-responsive element has at least 98% homology to SEQ ID NO: 12, at least 99% homology to SEQ ID NO: 12, or is SEQ ID NO: 12.

23. The genetically engineered lactic acid bacterial cell of claim 1, wherein the agent-responsive element has at least 98% homology to SEQ ID NO: 13, at least 99% homology to SEQ ID NO: 13, or is SEQ ID NO: 13.

24. The genetically engineered lactic acid bacterial cell of claim 1, wherein the agent-responsive element has at least 98% homology to SEQ ID NO: 14, at least 99% homology to SEQ ID NO: 14, or is SEQ ID NO: 14.

25. The genetically engineered lactic acid bacterial cell of claim 1, wherein the agent-responsive element has at least 98% homology to SEQ ID NO: 15, at least 99% homology to SEQ ID NO: 15, or is SEQ ID NO: 15.

\* \* \* \* \*